(12) United States Patent
Zhong

(10) Patent No.: US 9,283,256 B2
(45) Date of Patent: Mar. 15, 2016

(54) **ANTIBACTERIAL COMPOSITION COMPRISING *SALVIA* EXTRACTS**

(75) Inventor: Zhong Zhong, Beijing (CN)

(73) Assignee: Botanic Century (Beijing) Co. Ltd., Beijing (CN)

( * ) Notice: Subject to any disclaimer, the term of this patent is extended or adjusted under 35 U.S.C. 154(b) by 239 days.

(21) Appl. No.: 12/738,229

(22) PCT Filed: Oct. 14, 2008

(86) PCT No.: PCT/GB2008/003490
§ 371 (c)(1),
(2), (4) Date: Jul. 29, 2010

(87) PCT Pub. No.: WO2009/050451
PCT Pub. Date: Apr. 23, 2009

(65) Prior Publication Data
US 2010/0292318 A1  Nov. 18, 2010

(30) Foreign Application Priority Data
Oct. 15, 2007 (CN) .......................... 2007 1 0163553
Jan. 15, 2008 (GB) .................................. 0801088.6

(51) Int. Cl.
*A61K 31/34* (2006.01)
*A61K 36/537* (2006.01)
*A61K 31/343* (2006.01)

(52) U.S. Cl.
CPC ............. *A61K 36/537* (2013.01); *A61K 31/343* (2013.01)

(58) Field of Classification Search
USPC ........................................................ 514/468
See application file for complete search history.

(56) References Cited

U.S. PATENT DOCUMENTS

| 5,604,262 A | * | 2/1997 | Wood ............................. 514/675 |
| 2003/0031690 A1 | | 2/2003 | Kang et al. |
| 2004/0191334 A1 | * | 9/2004 | Shaw et al. ..................... 424/746 |
| 2005/0148495 A1 | * | 7/2005 | Lambert et al. ..................... 514/2 |

FOREIGN PATENT DOCUMENTS

| CN | 1143498 | | 2/1997 |
| CN | 1317308 | | 10/2001 |
| CN | 1394870 | | 2/2003 |
| CN | 1518985 A | * | 8/2004 |
| CN | 1670019 | | 9/2005 |
| CN | 1927265 | | 3/2007 |
| CN | 1944455 | | 4/2007 |
| CN | 101073599 | | 11/2007 |
| WO | WO2004084884 | | 10/2004 |

OTHER PUBLICATIONS

"Antibiotic resistance in Gram-positive bacteria: epidemiological aspects" by Witte, J. Antimicrob. Chemother. 44 (Topic A), 1-9 (1999).*
"PF2401-SF, Standardized fraction of Savia miltiorrhiza and its constituents, tanshinone I, tanshinone IIA, and cryptotanshinone, protect primary cultured rat hepatocytes from bile acid-induced apoptosis by inhibiting JNK phosphorylation"; Food and Chemical Toxicology, Pergamon, GB, vol. 45, No. 10, Aug. 12, 2007, pp. 1891-1989, XP022196748; ISSN: 0278-6915; p. 1892, paragraph 2.2, p. 1893, paragraph 3.1.
Tian G et al: Separation of tanshinones from Salvia miltiorrhiza Bunge by multidimensional counter-current chromatography; Journal of Chromatography; Elsevier Science Publishers B.V. Amsterdam, NL, vol. 945, No. 1-2, Feb. 1, 2002, pp. 281-285, XP004333356; ISSN: 0021-9673; abstract; p. 282, paragraph 2.3; p. 283.
Analytica Chimica Acta, vol. 589, No. 2, Apr. 2007, "Coupling continuous ultrasound-assisted extraction with ultrasonic probe, solid-phase extraction and high-performance liquid chromatography for the determination of sodium Danshensu and four tanshinones in Salvia miltiorrhiza bunge"; pp. 231-238; Qiao Yang.
Database EPODOC; European Patent Office, The Hague, NL; "Method of separating and purifying tanshinone" XP002513685 abstract; Beijing Tianchun Weitong Biolo; Feb. 5, 2003.
Database CAPLUS; Chemical Abstracts Service, Columbus, Ohio, US; Fang, Chi-Nien et al: "The antibacterial components of Dan-Shen" XP002513686; Database accession No. AN: 1978:177078 abstract & Xuaxue Xuebao, vol. 34, No. 3, 1976, pp. 197-209.
Database CAPLUS; Chemical Abstracts Service, Columbus, Ohio, US; Gao, Yu-Gui et al: "Pharmacology of tanshinone" XP002513687; Database accession No. AN: 1980:69509 abstract & Yaoxue Xuebao; vol. 14, No. 2, 1979, pp. 75-82.
Database WPI Week 200478; Thomas Scientific, London, GB; AN: 2004-785288; XP002513688 & CN 1518985A (Huatuo Medicine Sci Tech Dev Co Ltd Shan) Aug. 11, 2004; abstract.
Database WPI Week 200062; Thomas Scientific, London, GB; AN: 2000-638914; XP002513689 & CN 1143498A (Zhan J) Feb. 26, 1997; abstract.

* cited by examiner

*Primary Examiner* — Rei-Tsang Shiao
(74) *Attorney, Agent, or Firm* — Dickinson Wright PLLC

(57) ABSTRACT

The present invention relates to a selectively purified tanshinone compounds containing extract from the root of a *Salvia* spp comprising Cryptotanshinone, Dihydrotanshinone, Tanshinone I, and Tanshinone IIA. It comprises at least 15%, by weight of the said identified tanshinone compounds and at least 4% by weight, of cryptotanshinone. The extract and formulations thereof have been found to exhibit excellent anti-microbial properties against, in particular MRSA.

20 Claims, 13 Drawing Sheets

1  2  3

1  2  3

1  2  3

1 to 19

1  2  3

1. Ethyl acetate extract of Danshen
2. Purified Tanshinone compounds
3. Mixed Tanshinone standard
   Bottom to top order:
   - Dihydrotanshinone,
   - Cryptotanshinone,
   - Tanshinone I and
   - Tanshinone IIA

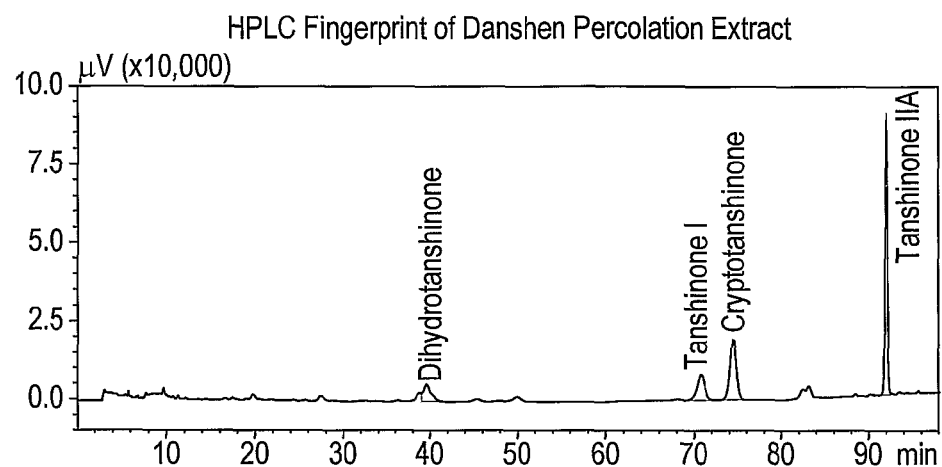
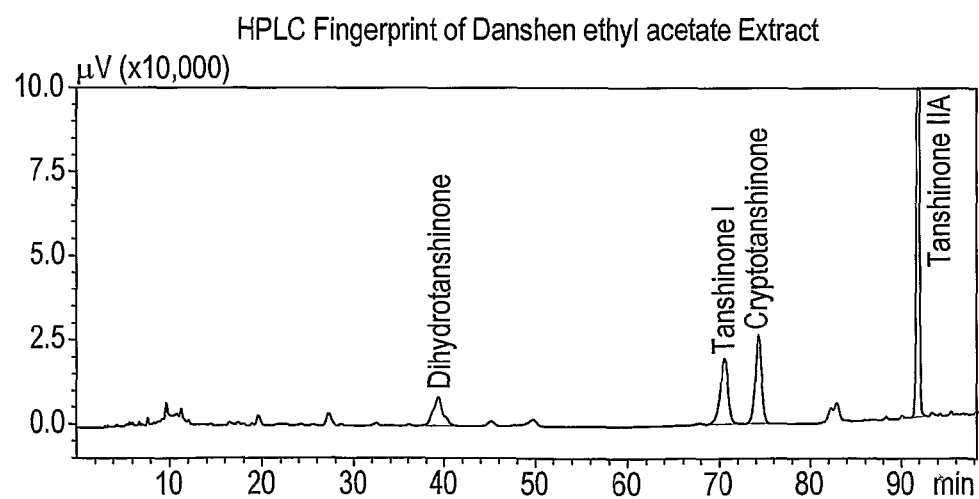

HPLC Fingerprint of Purified Tanshinones Extract

HPLC Fingerprint of Reference compounds

Where:
1. is JZ0702
2. is mixed references

The markers - bottom to top are:
• Dihydrotanshinone
• Cryptotanshinone
• Tanshinone I and
• Tanshinone IIA

ANTIBACTERIAL COMPOSITION COMPRISING *SALVIA* EXTRACTS

TECHNICAL FIELD OF THE INVENTION

The present invention relates to an antibacterial botanical product and more particularly to a selectively purified tanshinone compounds containing extract which exhibits activity against, in particular:

Methicillin resistant *Staphylococcus aureus* (MRSA),
Methicillin susceptible *Staphylococcus aureus* (MSSA),
Coagulase negative Staphylococci (CNS), and
*Streptococcus*, inparticular, *Steptococcus pneumoniae*.

The extract also demonstrates activity against *Propionibacterium acnes* and thus may be used therapeutically or cosmetically for the treatment of acne.

The invention also relates to a scalable method of extraction including purification, formulations of said extracts and methods of treatment.

BACKGROUND OF THE INVENTION

The extract exhibiting these beneficial properties is derived from the root and rhizome of *Salvia miltiorrhiza* Bunge, a perennial herb from the Labiatae family. In Traditional Chinese Medicine (TCM) it is also referred to as Danshen.

Danshen was recorded as a top-grade herbal medicine in Shennong's Classic of Materia Medica, as well as in Compendium of Materia Medica and Annotations to the Divine Husbandman's Classic of Materia Medica.

It has broad clinical applications.

In the medical monographs of Coverage of the Materia Medica, Compendium of Materia Medica and Renewal of Herbal, Danshen is said to evacuate puss with detoxication, a reference to its anti-bacterial and anti-inflammatory effects.

It should be noted that in TCM whole extracts, usually obtained as decoctions, are typically used in combination with a number of other herbs.

Modern scientific research on Danshen started in 1930's.

The chemical constituents of Danshen can be divided into two main categories of chemicals:

lipid-soluble, and
water-soluble.

Earlier studies on "active" compounds of Danshen have mainly been concentrated on the lipid-soluble compounds, where around 40 compounds have been found so far. These can be further divided into two groups:

Tanshinones (o-quinone structure) and
Rosiglitazones (o-hydroxy rosiglitazone, paraquinoid structure).

Most of the tanshinone compounds are diterpenes, of which they are mainly diterpene quinones.

Studies on Lipid-Soluble Chemicals

Over 40 different compounds have been identified, including, for example: tanshinone, cryptotanshinone, tanshinone IIA, tanshinone IIB, methyltanshinone, hydroyltanshinone IIA, isotanshinone I, isotanshinone II, isocryptotanshinone, miltirone, L-dihydrotanshinone I, neotanshinone A, B, C, and salviol.

The structures of a few of these compounds are illustrated below:

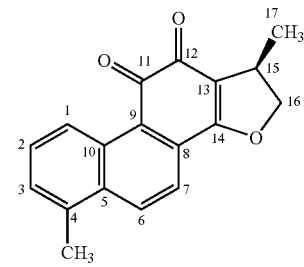

Dihydrotanshinone

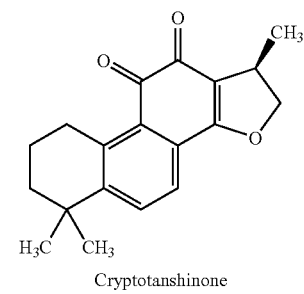

Cryptotanshinone

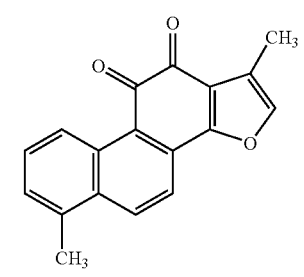

Tanshinone I

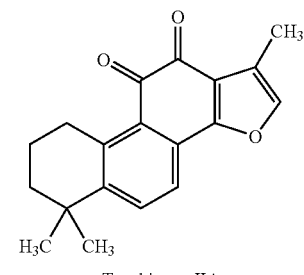

Tanshinone IIA

Antimicrobial and Anti-Inflammation Effects

The early research on the lipid soluble compounds of Danshen focused on its antimicrobial effects and a series of screens on anti-bacterial, anti-fungi and anti-tubercle bacillus were carried out by the Institute of Materia Medica, Chinese Academy of Medical Sciences. The screen results showed that the total tanshinones significantly inhibited *Staphylococcus aureus* and an inhibition zone still appeared on sensitive strain 209P at the low concentration (6.25 µg/per tablet) on filter paper disc. The test on 50 erythromycin-resistant *Staphylococcus aureus* isolates from the clinic also showed activity.

A test comparing the activity of tanshinone and 10 antibiotics has been carried out and the results showed that *Staphylococcus aureus* which was resistant to antibiotics was susceptible to tanshinone.

With filter paper disc, 5 out of 10 chemicals isolated from Danshen demonstrated anti-*Staphylococcus aureus* activity. These chemicals were:
Cryptotanshinone,
Dihydrotanshinone,
Hydroyltanshinone,
Tanshinone IIB, and
Methyltanshinone.

Tanshinone IIA, tanshinone I, and neotanshinone A, B, and C did not show activity.

A study on the anti-microbial activity of tanshinone HA, and its correlation with the solvent selection, was carried out by ZHU Jiarong et al. When tanshinones were dissolved in chloroform tanshinone IIA did not demonstrate any anti-microbial activity but when it was dissolved in dimethylformamide (DMF) tanshinone IIA and IIB showed activity against:
*Escherichia coli* at the minimum inhibitory concentration (MIC) 50 or 25 µg/ml,
*Staphylococcus aureus* ATCC225923 with MIC 100 or 50 µg/ml,
*Bacillus aeruginosus* ATCC227853 with MIC 50 or 25 µg/ml, and
*Haemolytic streptococcus* with MIC 121.5 or 25 µg/ml.

LUO Houwei et al reported tanshinone and 42 related compounds were tested against *Tubercle bacillus* in a structure-activity correlation study. It demonstrated that the quinone group was the principle structure responsible for the activity. 19 compounds with quinone group isolated from Danshen showed potent anti-bacterial activity and the MIC ranged between 0.31-5 mg/l. The bacteriostasis activity of o-quinone compounds was stronger than that of p-quinone compounds. A-ring hydroxylation or dehydrogenation of the inter ring resulted in less bacteriostasis activity. Different substitutions at a-H furan ring of tanshinone clearly affected bacteriostasis activity.

L I Jiangqin et al. reported the study on tanshinone IIA, cryptotanshinone and their zinc iron complex against *Escherichia coli* and *Staphylococcus aureus* activity. Compared with each other, cryptotanshinone was more potent than tanshinone IIA. Cryptotanshinone showed better inhibition effect against *Staphylococcus aureus* than *Escherichia coli*. The bacteriostasis activity was enhanced when cryptotanshinone complex was formed with metal ions, especially with zinc.

LUO Yongjian et al reported that a bacteriostasis experiment was carried out on a product called "Xiao Yan Kun" which was extracted from Gansu Danshen. The main compounds of the product were cryptotanshinone and tanshinone IIA. In the test, acetone was used as solvent and berberine and oxytetracycline were used as the positive controls. The bacterial stains included *Staphylococcus aureus, Bacillus subtilis, Streptococcus agalactiae, Pseudomonas aeruginosa, Escherichia coli*, and *Streptococcus dysgalactiae*, respectively. The test samples showed better activity against *Staphylococcus aureus, Bacillus subtilis* and *Streptococcus agalactiae* than that of berberine. Cryptotanshinone was more active than tanshinone IIA but both samples were less active than oxytetracycline. Both samples showed no effect on *Pseudomonas aeruginosa, Escherichia coli* and *Streptococcus dysgalactiae*.

The patent literature makes reference to a number of Salviae extracts.

CN101073599 discloses an extract of total ketone of comprising cryptotanshinone, tanshinone I, tanshinone IIA, methyl tanshinon, dihyderotanshinon I and ramification for use as a medicine or food.

CN1927265 discloses a process for increasing cryptotanshinone content in Salviae miltoiorrhizae extract.

CN1670019 discloses a method for extracting tanshinone in which a first extraction gives cryptotanshinone and dihydrotanshinone and a second extraction gives tanshinone IIA and tanshinone I.

CN1944455 discloses a method of increasing the content of cryptotanshinone, dihydrotanshinone, tanshinone IIA and tanshinone I using column chromatography with a given simultaneous solvent extraction.

None of the above specifically disclose an extract as characterized by the claims of the present invention.

Additional prior art includes:
US2003/0031690 which discloses a cosmetic composition comprising cryptotanshinone which is said to inhibit 5 alpha reductase activation. KR20020028041 which discloses the use of a composition containing Salviae miltoiorrhizae extract to treat pimples based on it's inhibition of 5 alpha reductase.

CN1317308 which discloses a cryptotanoshine containing cream to treat acne.

Biosci Biotechnol. Biochem 63 (12) 2236-2239 suggests that superoxidase radical formation might be the cause of the antibacterial activity of cryptotanshinone, dihydrotanshinone I.

More recently, in the Journal of Microbiology, August 2007 p350-357 it has been reported that *Salvia miltiorrhiza* shows anti-microbial activity against MRSA. Different extracts were studied, including methanol, hexane, chloroform, ethyl acetate, butanol and water. The best activity was found in hexane and chloroform fractions. MIC for the hexane fraction against various MRSA specimens was 64<MIC's>128 µg/ml.

With drug resistance proving such a major problem today, any active medicines or bactericidal compositions would be highly desirable.

It is an aim of the present invention to provide a medicine or bactericidal compositions which is/are effective against MRSA in low doses and which can be produced effectively on a commercial, as opposed to laboratory scale.

SUMMARY OF THE INVENTION

According to a first aspect of the present invention there is provided a selectively purified tanshinone compounds containing extract from the root of a *Salvia* spp comprising:
Cryptotanshinone,
Dihydrotanshinone,
Tanshinone I, and
Tanshinone IIA,
characterized in that the above identified tanshinone compounds comprise at least 15%, by weight, of the selectively purified extract and the cryptotanshinone comprises at least 4%, by weight, of the selectively purified extract.

Preferably, the *Salvia* spp is *Salvia miltiorrhiza* Bunge although other *Salvia* Spp such as
*Salvia apiana*
*Salvia argentea*
*Salvia arizonica*
*Salvia azurea*
*Salvia carnosa*
*Salvia clevelandii*
*Salvia coccinea*
*Salvia divinorum*
*Salvia dorrii*
*Salvia farinacea*
*Salvia forreri*

*Salvia fulgens*
*Salvia funerea*
*Salvia glutinosa*
*Salvia greggii*
*Salvia guaranitica*
*Salvia hispanica*
*Salvia leucantha*
*Salvia leucophylla*
*Salvia libanotica*
*Salvia longistyla*
*Salvia lyrata*
*Salvia mexicana*
*Salvia officinalis.*
*Salvia patens*
*Salvia polystachya*
*Salvia potus.*
*Salvia pratensis*
*Salvia roemeriana*
*Salvia sclarea*
*Salvia spathacea*
*Salvia splendens*
*Salvia verticillata*
*Salvia viridis*
may be used.

More preferably still the identified tanshinone compounds comprises at least 35%, by weight, of the selectively purified extract and the cryptotanshinone comprises at least 15%, by weight, of the selectively purified extract.

Yet more preferably still the identified tanshinone compounds comprise at least 45%, by weight, of the selectively purified extract and the cryptotanshinone comprises at least 25% by weight, of the selectively purified extract.

In one embodiment the cryptotanshinone comprises at least 20%, more preferably at least 25%, more preferably still at least 40% and maybe as much as 60% of the four identified tanshinone compounds.

Similarly, the tanshinone IIA preferably comprises less than 55% of the four identified tanshinone compounds, more preferably still less than 50%, yet more preferably still less than 40% and may comprise as little as 20% or less of the four identified tanshinone compounds.

In a preferred embodiment, the selectively purified tanshinone compound containing extract is characterized in that it comprises the four identified tanshinone compounds in an amount of 42.89% (plus or minus 40%, through 30% to 20%):
  a cryptotanshinone content of 18.95% (plus or minus 40%, through 30% to 20%),
  a dihydrotanshinone content of 3.65% (plus or minus 40%, through 30% to 20%),
  a tanshinone I content of 3.82% (plus or minus 40%, through 30% to 20%), and
  a tanshinone IIA content of 16.47% (plus or minus 40%, through 30% to 20%).

The selectively purified tanshinone compound containing extract may be characterized in that it has an HPLC fingerprint substantially as illustrated in FIG. 13 with characteristic peaks as indicated.

The extract may be used in the manufacture of an antibacterial medicament, more particularly one for use in the treatment of a drug resistant bacterium. It is particularly useful to treat:
  Methicillin resistant *Staphylococcus aureus* (MRSA),
  Methicillin susceptible *Staphylococcus aureus* (MSSA),
  Coagulase negative Staphylococci (CNS), and
  *Streptococcus*, in particular, *Steptococcus pneumoniae*.

It may also be used in the medical or cosmetic treatment of acne, a skin condition caused by infection with *Propionibacterium acnes*.

The extract may be included as the active ingredient of a pharmaceutical or cosmetic formulation with one or more excipients. It may also be added to a carrier to form compositions, e.g. hand cleaning or surface cleaning compositions which may take the forms of solutions, gels, sprays and impregnated wipes.

Preferred pharmaceutical or cosmetic formulations are for topical or oral delivery.

An effective concentration can be less than 64 µg/ml, more particularly less than 32 µg/ml and as low as 16 µg/ml or lower. Levels of activity at such low concentrations show a significant improvement over, for example, the teaching in The Journal of Microbiology, August 2007 p350-357.

According to a further aspect of the present invention there is provided a scalable method of manufacturing a selectively purified tanshinone compounds containing extract of the root of a *Salvia* spp comprising the steps of:
  soaking raw material in strong ethanol for a time sufficient to solublize the tanshinone compounds,
  extracting the tanshinone compounds containing fraction using a percolation method, and
  concentrating the desired fraction under vacuum and recovering the ethanol.

Preferably the method further comprises one or more purification steps to concentrate the tanshinone compounds containing fraction and/or cryptotanshinone.

In one embodiment a first purification step comprises:
  a. dissolving the extract in sufficient water,
  b. allowing the desired fraction to precipitate out,
  c. discarding the aqueous solution, and
  d. collecting the precipitate.

In the preferred embodiment, a second purification step is conducted, comprising a separation on a macroporous resin column. This second purification step comprises:
  a) dissolving the precipitate in a mid strength ethanol; loading it onto an AB 8 macroporous resin column, manufactured by Lioayuan New Materials Ltd, (or other suitable column),
  b) adding further mid strength ethanol to wash the column, discarding the eluent, and
  c) eluting the desired extract with a higher than mid strength ethanol.

Preferably the mid strength ethanol is 60% strength and the eluting ethanol is 70% ethanol.

The invention will be further described, by way of example only, with reference to the following examples in which.

Figure 5A:
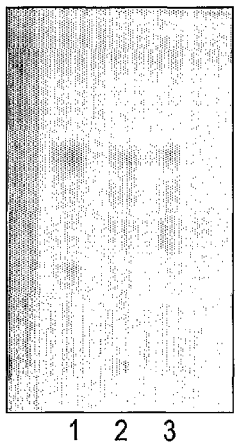
Figure 5B:
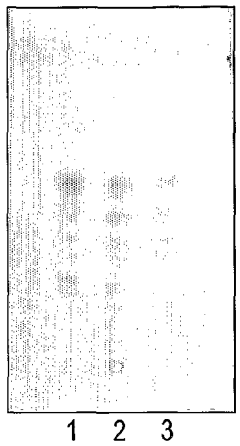
Figure 5C:
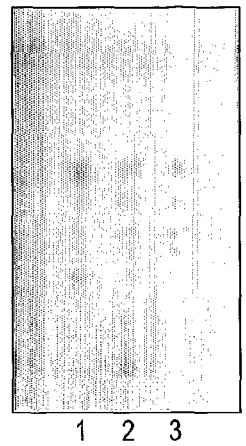
Figure 6:
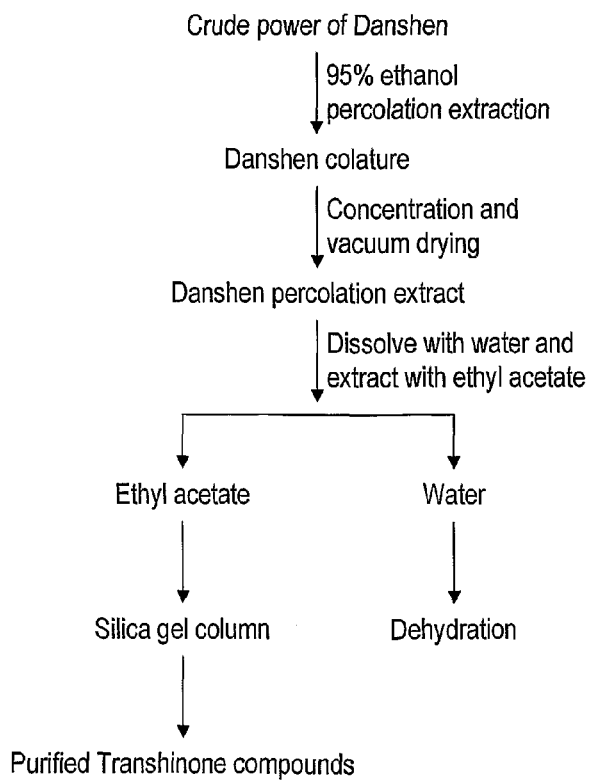
Figure 7:
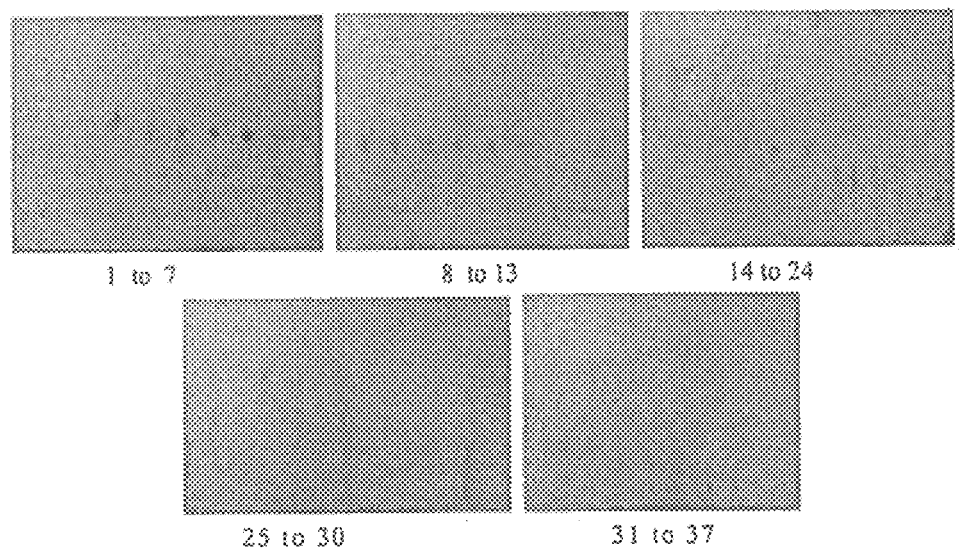
Figure 8:
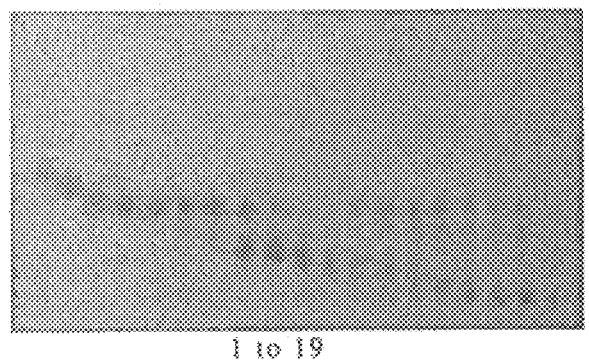
Figure 9:
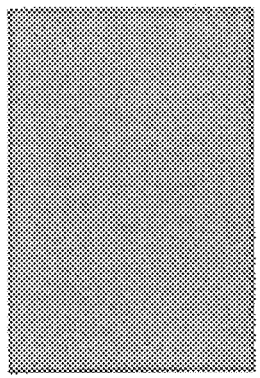
Figure 10C:
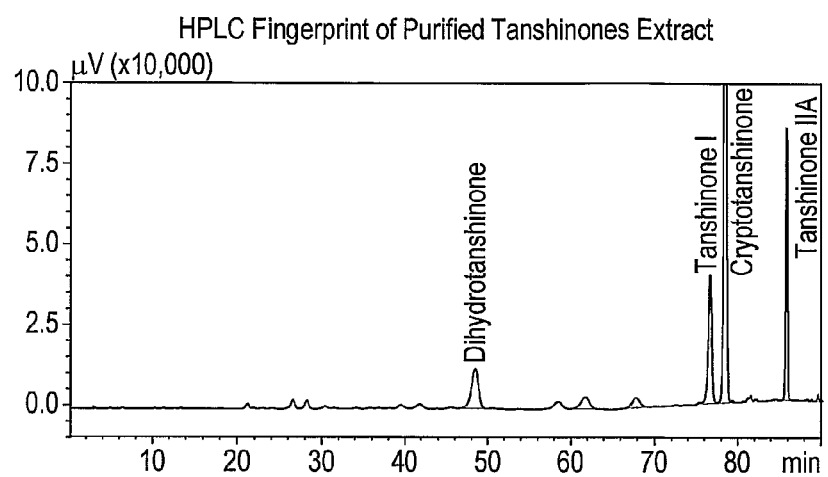
Figure 10D:
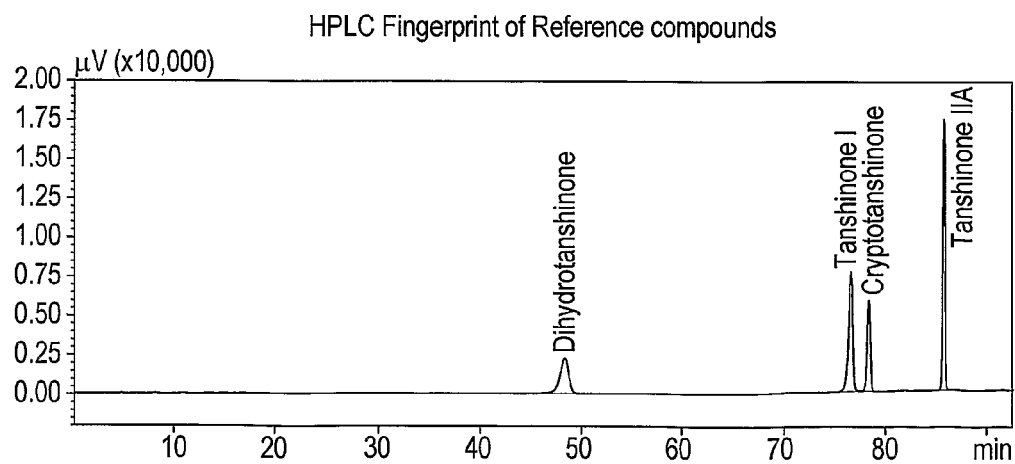
Figure 11:
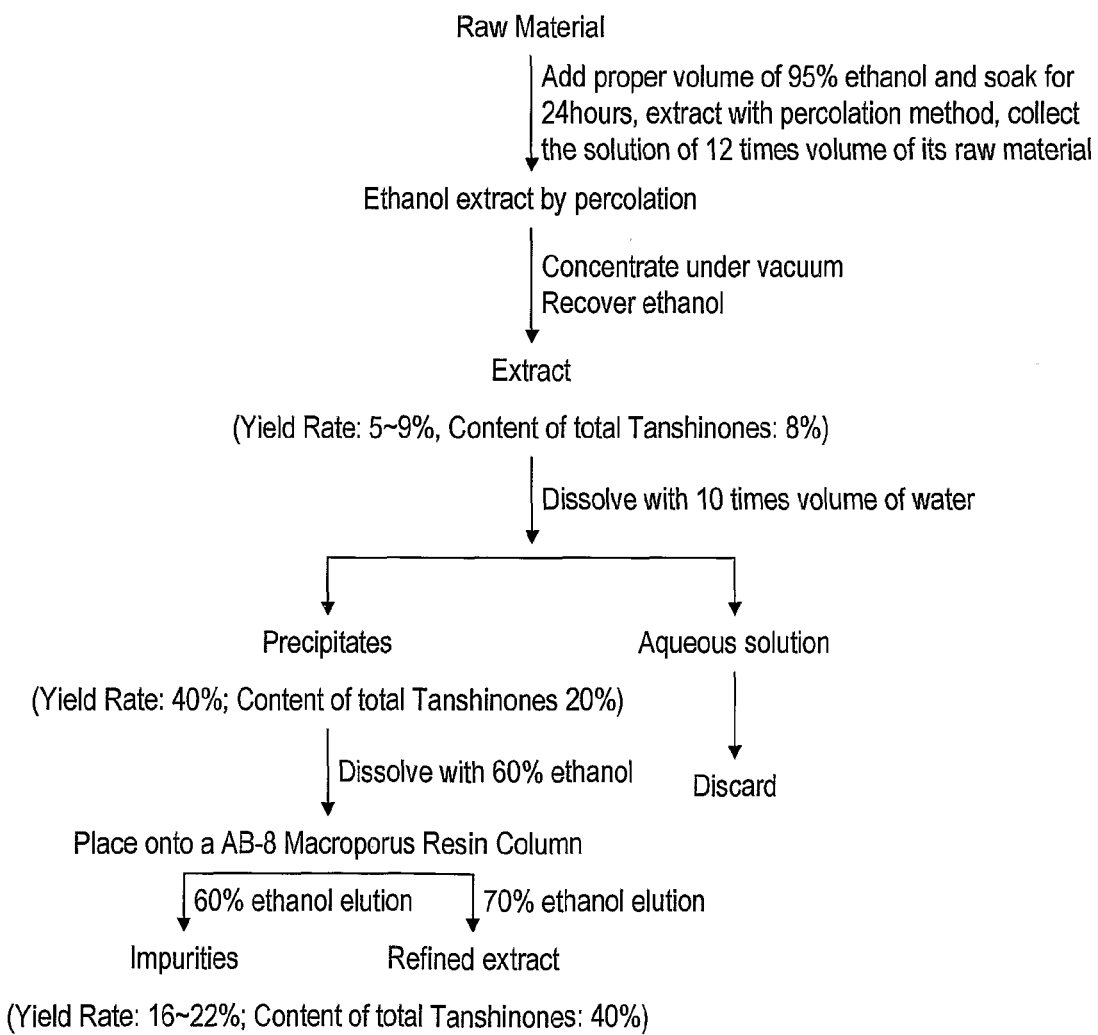
Figure 12:
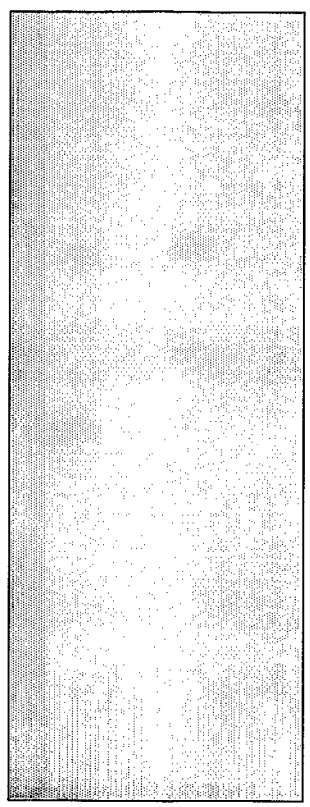
Figure 13:
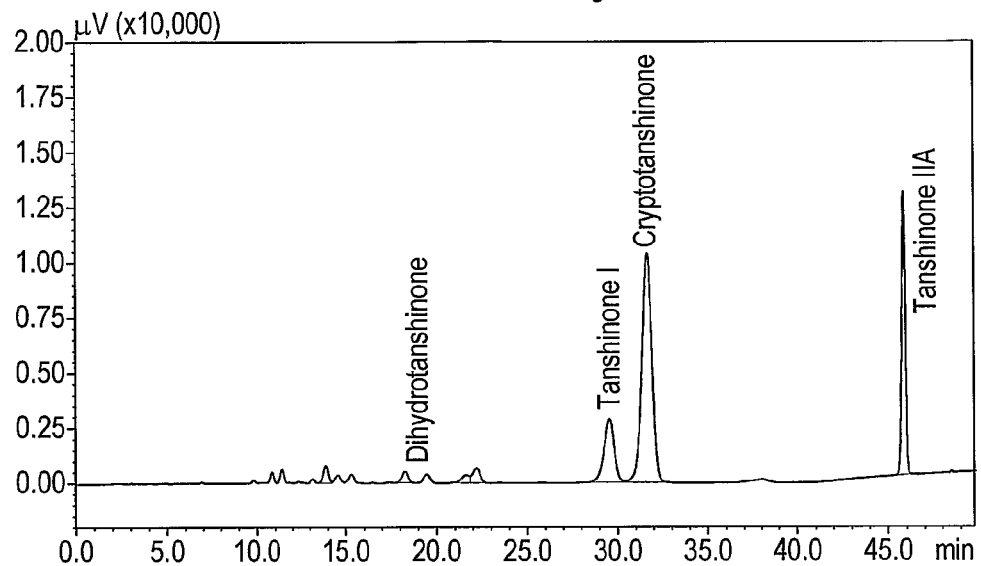
Figure 14:
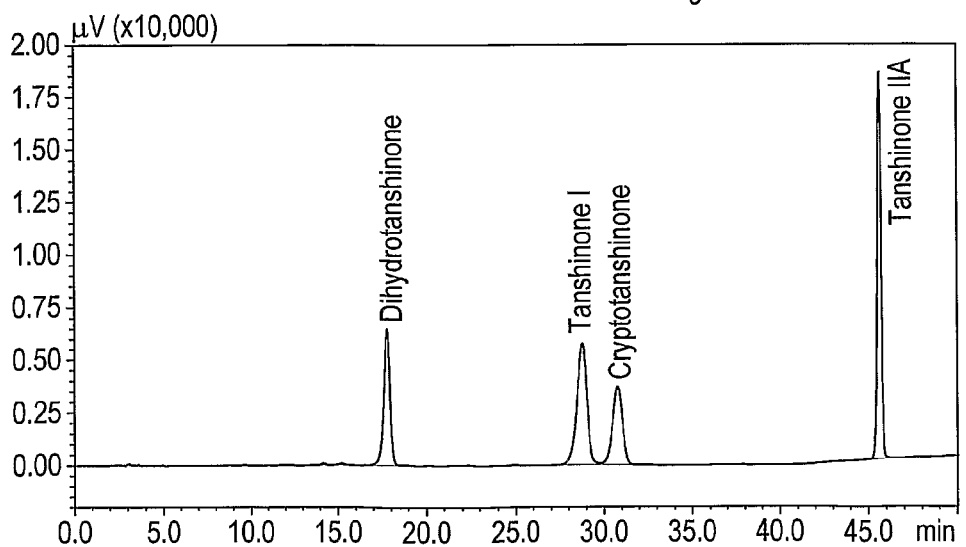
Figure 15:
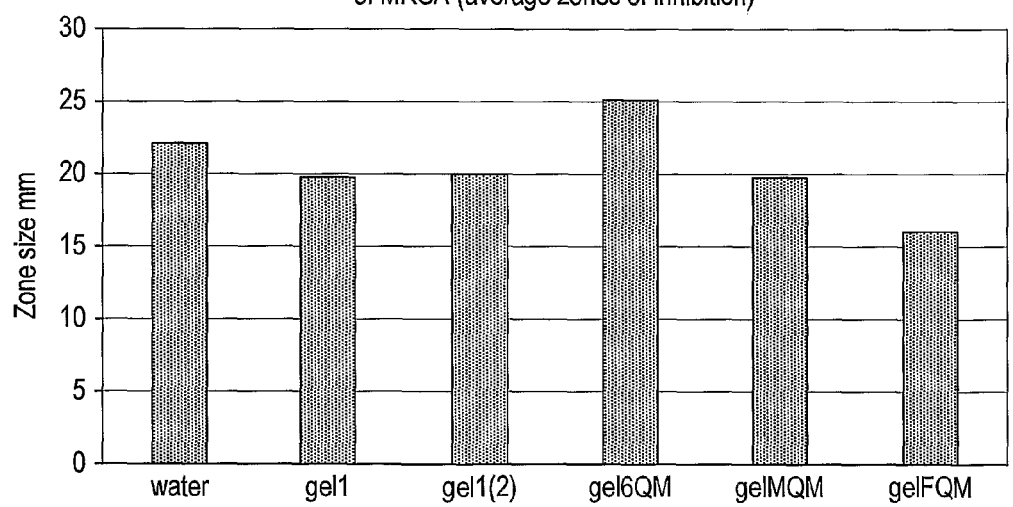

FIGS. 5a-c are TLC fingerprints in which lane 1 is a $CO_2$ extract, lane 2 is an ethyl acetate extract and lane 3 is a referenced sample containing (bottom to top) dihydrotanshinone, cryptotanshinone, tanshinone I, and tanshinone IIA;

FIG. 6 is a flow diagram illustrating an improved extraction process;

FIG. 7 is a TLC fingerprint showing (from left to right and top to bottom) 37 consecutive silica gel purified fractions from the process illustrated in FIG. 6;

FIG. 8 is a TLC fingerprint showing (from left to right) 19 variously combined silica gel purified fractions from the process illustrated in FIG. 6;

FIG. 9 is a TLC fingerprint showing (from left to right) the 7$^{th}$ to 13$^{th}$ merged silica gel purified fractions from FIG. 8 (JZ061);

FIG. 10*a* is an HPLC chromatogram of a percolation extract under conditions as set out in Table 3 (gradient 1) (SL0601);

FIG. 10*b* is an HPLC chromatogram of an ethyl acetate purified extract under conditions as set out in Table 3 (gradient 1) (YY0601);

FIG. 10*c* is an HPLC chromatogram of a silica gel purified extract under conditions as set out in Table 3 (gradient 1) (JZ0601);

FIG. 10*d* is an HPLC chromatogram of reference compounds under conditions as set out in Table 3 (gradient 1);

FIG. 11 is a flow diagram illustrating a scalable extraction process giving a characterized product rich in cryptotanishone as per section 6.0;

FIG. 12 is a TLC fingerprint in which lane 1 is an extract from the process described with reference to FIG. 11 and lane 2 is a mixed reference samples from bottom to top dihydrotanshinone, cryptotanshinone, tanshinone I, and tanshinone IIA;

FIG. 13 is an HPLC chromatogram of an extract from the process described with reference to FIG. 11 under conditions as set out in Table 4 (gradient 2);

FIG. 14 is an HPLC chromatogram of reference compounds under conditions as set out in Table 4 (gradient 2); and FIG. 15 is a table showing the activity of a number of gel formulations.

In the HPLC figs the identified compound peaks read left to right are: dihydrotanshinone, tanshinone I, cryptotanshinone, and tanshinone IIA.

DETAILED DESCRIPTION 1.0 Extraction Methodology

In order to identify selectively purified tanshinone compound containing extracts from the root of a *Salvia* spp, a number of alternative methodologies were examined.

Initially, a super critical fluid extraction (SCFE) and an ethyl acetate extraction (EAE) were conducted:

1.1 SCFE

Put the pulverized dry raw material of *Salvia miltiorrhiza* into the SCE-CO2 extractor. Set up the pressure at 20 MPa and temperature at 45 degree C. Add 30% (relative to the raw material) ethanol (95%) as the entrainer to the system. Set the flow rate at 1 ml/min and continuously extract for 60 min. The dark red crystal obtained was code numbered SME-1.

1.2 EAE

Figure 1:
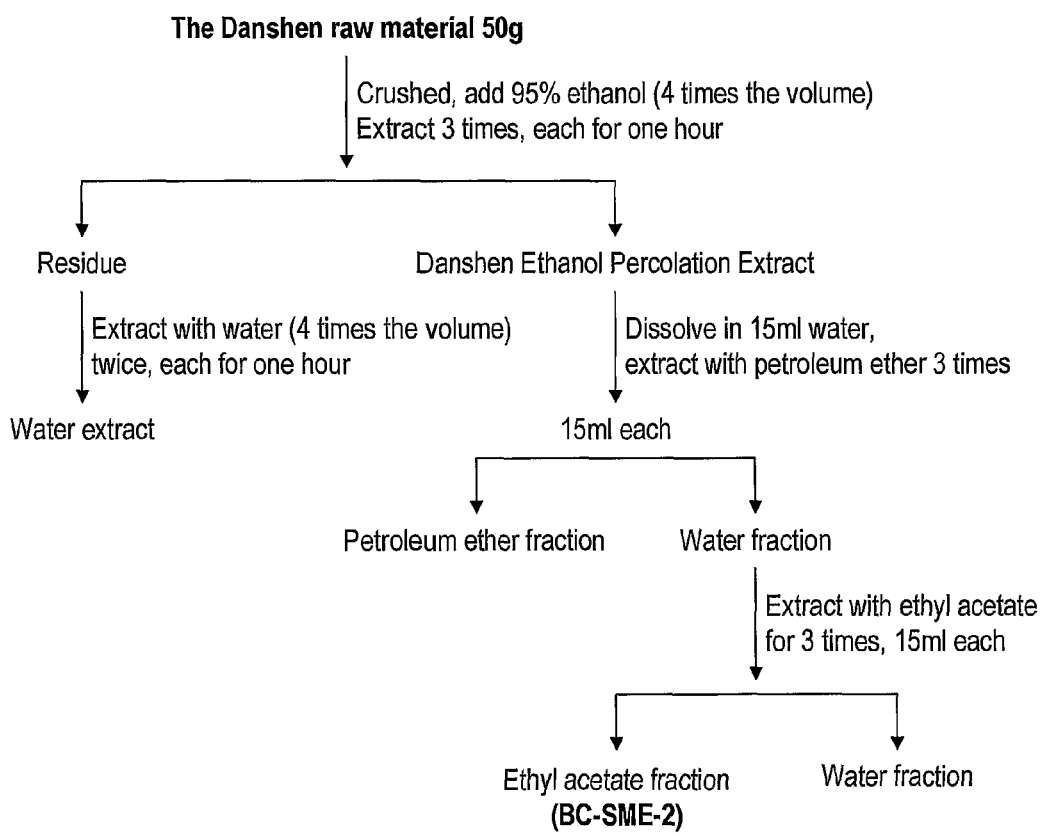
FIG. 1 is a flow diagram illustrating an ethyl acetate extraction process.

The EAE methodology used is that set out with reference to FIG. 1.

The Danshen raw material (50 g) is crushed and subjected to an ethanol extraction with 95% ethanol (added to four times volume) and left for about 1 hour. The process was repeated 3 times and the solvent extracts combined.

Any residue was subjected to a water extraction (added to four times volume) and left for about an hour. Repeat twice.

The ethanol extract underwent a percolation extraction in which the extract was dissolved in 15 ml of water and extracted with petroleum ether. The process was repeated three times adding 15 ml of water each time.

The water fraction was then extracted with ethyl acetate (15 ml), and the process repeated three times. The resulting ethyl acetate fraction is referred to generally as SME-2.

2.0 Testing

The resulting extracts were tested for their antimicrobial activity by the National Institute for the Control of Pharmaceutical and Biological Products (NICPBP), National Center for Drug Resistance of Bacteria Beijing, PR China.

Results:

The extracts were tested for antimicrobial activity against 401 strains, over 95% of which were clinical isolates with drug resistance including 41 strains of MRSA and 17 strains of MRCNS.

The pre-experiment showed that BC-SME-2 had:
a high activity against Gram-positive bacteria, and
a low activity against Gram-negative bacteria with a strong selective antibacterial action.

The samples showed a strong antibacterial action against BOTH
MRSA, and
MRCNS.

The samples had a strong action against *Staphylococcus aureus* and *Staphylococcus epidermidis*.

The information and numbers of the tested strains are listed in Table 1 and the MIC50 value and range for the important strains are listed in Table 2.

TABLE 1

Test strains and results

| Name of Bacteria | Nos. | Average MIC50 (µg/ml) |
|---|---|---|
| *Enterococcus faecalis* | 72 | >512 |
| *Enterococcus* sp. | 5 | >512 |
| *Escherichia coli* | 4 | >512 |
| *Staphylococcus aureus* | 120 | 24 |
| *Staphylococcus epidermidis* | 120 | 22 |
| *Streptococcus pneumoniae* | 43 | 47 |
| *Klebsiella pneumoniae* ss. | 1 | 16 > 512 |
| *Pseudomonas aeruginosa* | 1 | >512 |
| *Streptococcus equi* | 1 | >512 |
| *Streptococcus equinus* | 1 | 128 |
| *Streptococcus equisimilis* | 1 | >512 |
| *Streptococcus iridans*, alpha-hem. | 5 | 64 |
| *Streptococcus*, beta-haem. Group A | 1 | 64 |
| *Streptococcus*, beta-haem. Group B | 2 | 256, 64 |
| *Streptococcus*, beta-haem. Group C | 2 | 64 |
| *Streptococcus*, beta-haemolytic | 15 | 32 > 512 |
| *Streptococcus* sp. | 6 | 256 |
| *Streptococcus* sp. | 1 | 256 |

TABLE 2

Value and range of MIC50 for the important bacteria strains

| Bacteria Name | Strains | IC50 (µg/ml) | MIC50 range (µg/ml) |
|---|---|---|---|
| *Staphylococcus aureus* | 120 | 16 | 2-1024 |
| *Staphylococcus epidermidis* | 120 | 16 | 1-1024 |
| *Enterococcus* sp. | 77 | 1024 | 16-1024 |

TABLE 2-continued

Value and range of MIC50 for the important bacteria strains

| Bacteria Name | Strains | IC50 (μg/ml) | MIC50 range (μg/ml) |
|---|---|---|---|
| *Streptococcus pneumoniae* | 43 | 32 | 16-1024 |
| *Streptococcus* sp. | 35 | 256 | 32-1024 |

3.0 Extract Analysis

HPLC and TLC chromatographic fingerprints of the active extracts were obtained as set out below:

3.1 HPLC Analysis 3.1.1 Samples

BC-SME 1 Batch No. CL0501 ($CO_2$ extract)

BC-SME 2 Batch No. YY0501 (Ethyl acetate extract)

3.1.2 Apparatus

Shimadzu LC-10A HPLC 3.1.3 Chromatographic conditions

Column: Atlantis® dC18 (5 μm, 250×4.6 mm)

Detection wavelength: 255 nm

Temperature: 25° C.

Flow Speed: 1 ml/min

Mobile phase: Methanol (A)-Water (B) gradient elution

Two differing gradients were used as set out in Tables 3 and 4.

TABLE 3

(Gradient 1)

| Time (min) | Mobile Phase A (%) | Mobile Phase B (%) |
|---|---|---|
| 0~55 | 63 | 37 |
| 55~75 | 63→70 | 37→30 |
| 75~95 | 70→90 | 30→10 |

TABLE 4

(Gradient 2)

| Time (min) | Mobile Phase A (%) | Mobile Phase B (%) |
|---|---|---|
| 0~35 | 70 | 30 |
| 35~45 | 70→100 | 30→0 |
| 45~50 | 100 | 0 |

Gradient 1 was the conditions used pre-experiment. Because of a long analytical period, Gradient 2 was found to be preferred.

3.1.4 Reagents

Methanol: chromatography pure, and Water: steam-distilled, the rest of reagents: analytical pure.

3.1.5 Reference Compounds

Dihydrotanshinone,

Cryptotanshinone,

Tanshinone I, and

Tanshinone IIA (for content assay only)

All supplied by National Institute for the Control of Pharmaceutical and Biological Products.

3.1.6 Preparation of Reference Solution

Measure precisely:

1 mg of Dihydrotanshinone, 1 mg of Cryptotanshinone, 1 mg of Tanshinone, and 2 mg of Tanshinone IIA, put them all into a 10 ml flask, add 8 ml of the mixed solution of methanol-methylene dichloride (9:1), ultrasound for 5 minutes, add the methanol-methylene dichloride (9:1) solution to volume, shake thoroughly and allow to stand.

3.1.7 Preparation of Sample Solution

Measure appropriate amount of BC-SME 1 ($CO_2$ extract) and BC-SME 2 (ethyl acetate extract) respectively, put them into two 10 ml flasks, add 8 ml of the methanol-methylene dichloride (9:1) solution, dissolve with ultrasound, add the methanol-methylene dichloride (9:1) solution to volume, shaking and filter. The subsequent filtrate was taken as a sample solution.

3.1.8 Sample Loading

Measure precisely 5 μl of each of the reference solution and the sample solution. Carry out the HPLC as described above.

3.1.9 The Experimental Results

According to the two gradient conditions mentioned above, the peaks of the different tanshinone indicators achieved baseline separation. Gradient 2 was used due to the advantage of a shorter detection time, and the saving of solution.

Figure 2A:
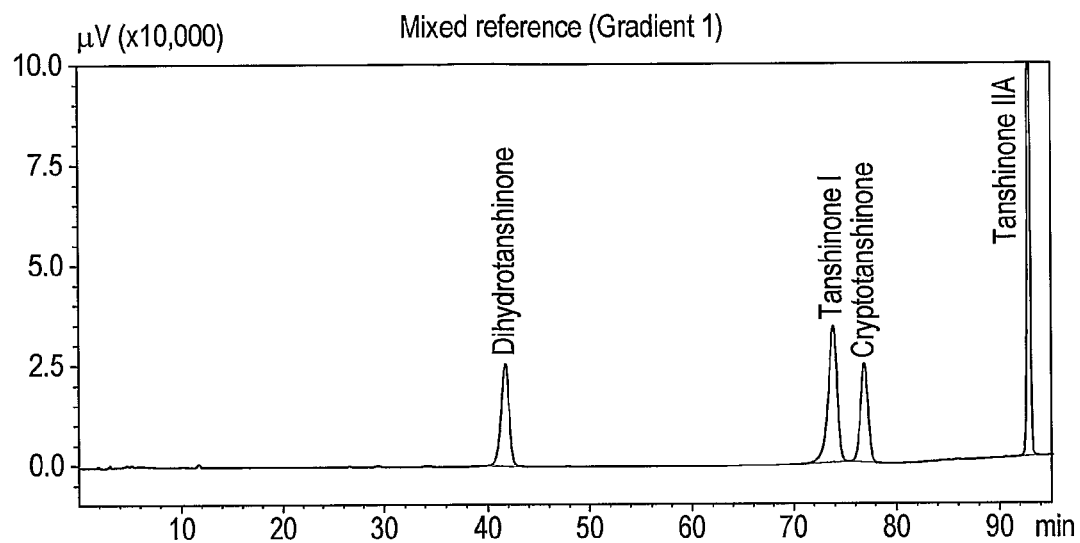
FIG. 2a is an HPLC chromatogram of reference samples under conditions as set out in Table 3 (gradient 1)
Figure 2B:
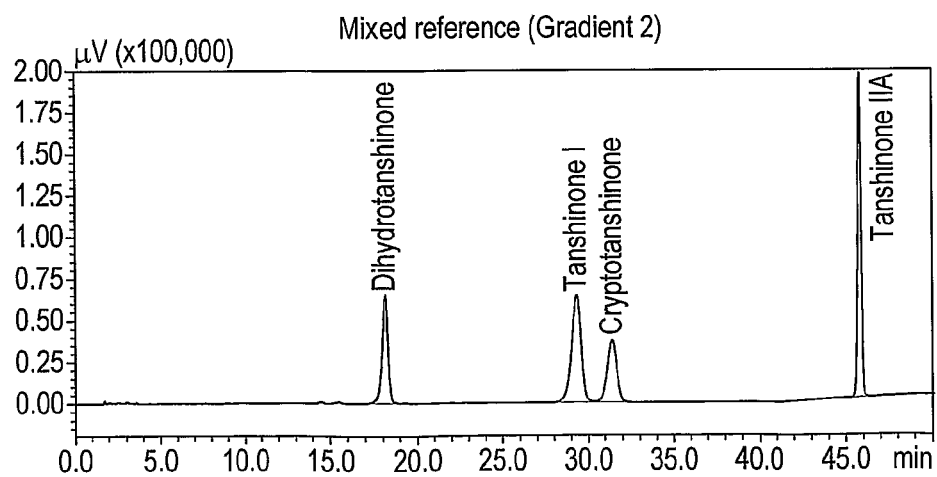
FIG. 2b is an HPLC chromatogram of reference samples under conditions as set out in Table 4 (gradient 2)
Figure 3A:
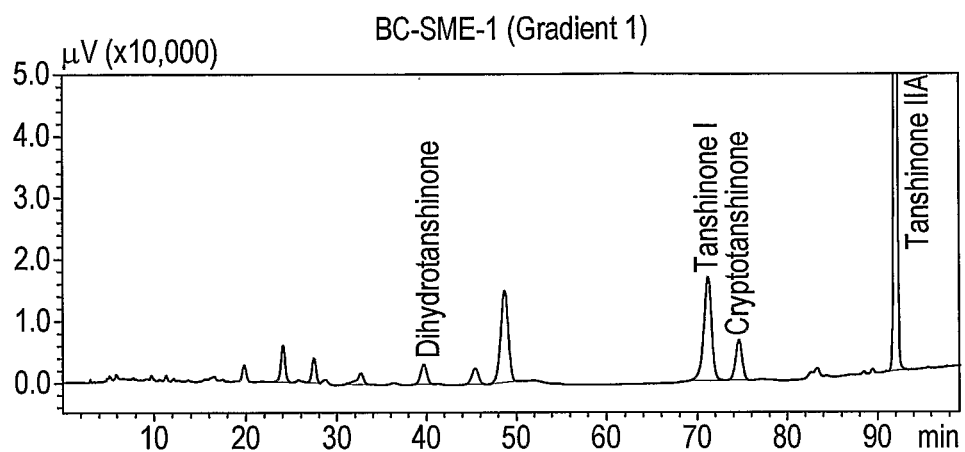
FIG. 3a is an HPLC chromatogram of a $CO_2$ extract under conditions as set out in Table 3 (gradient 1)
Figure 3B:
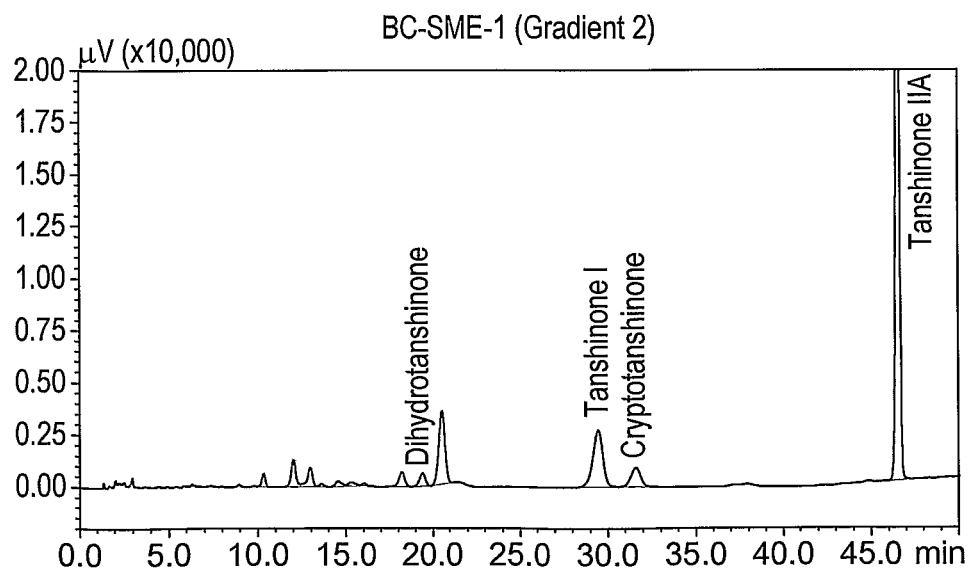
FIG. 3b is an HPLC chromatogram of a $CO_2$ extract under conditions as set out in Table 4 (gradient 2)
Figure 4A:
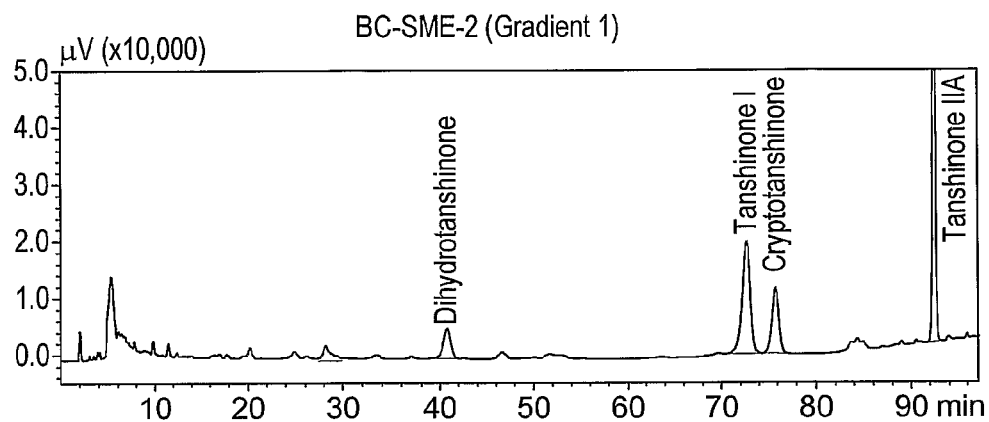
FIG. 4a is an HPLC chromatogram of ethyl acetate extract under conditions as set out in Table 3 (gradient 1)
Figure 4B:
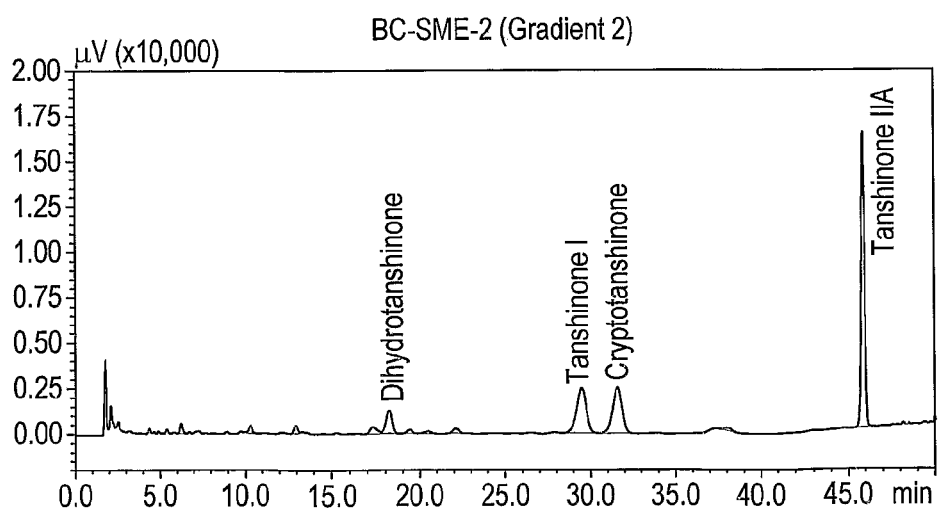
FIG. 4b is an HPLC chromatogram of ethyl acetate extract under conditions as set out in Table 4 (gradient 2)

The HPLC fingerprints of the referent samples are shown in FIGS. 2*a* and FIG. 2*b* (under the different gradient conditions) and those of the two extracts are shown with reference to FIGS. 3*a* and 3*b* (BC SME I) and FIGS. 4*a* and 4*b* (BC SME II). From Left to Right the peaks are:

Dihydrotanshinone,

Tanshinone I,

Cryptotanshinone, and

Tanshinone IIA.

The content assay for the samples is given in Table 5 below. (Gradient 1 was used for the content assay.)

TABLE 5

Content Assay

| Name | BC-SME-1 Content (%) | BC-SME-2 Content (%) |
|---|---|---|
| Dihydrotanshinone | 1.04 | 1.44 |
| Tanshinone I | 5.26 | 4.64 |
| Cryptotanshinone | 2.75 | 3.74 |
| Tanshinone IIA | 39.40 | 8.56 |
| Total: | 48.45 | 18.38 |

3.1.10 Discussion

From the HPLC content assay, it was found that the total tanshinone content was 48.5% in BC-SME 1, much higher than that in BC-SME 2. This result can explain the dissolvability difference of the two samples in polar solvents.

The content of tanshinone IIA was as high as 39.40% in BC-SME 1, but the antibacterial activity level was low.

The contents of dihydrotanshinone and cryptotanshinone in BC-SME 2 were higher than those in BC-SME 1, so it is presumed that the better antibacterial activity level of BC-SME 2 is due to the presence of these compounds.

3.2 TLC Analysis 3.2.1 Samples

BC-SME 1 Batch No: CL0501

BC-SME2 Batch No: YY0501

3.2.2 Standards and Reagents

Dihydrotanshinone,
Cryptotanshinone,
Tanshinon I, and
Tanshinone IIA.

All supplied by National Institute for the Control of Pharmaceutical and Biological Products.

Methanol: chromatographic pure (US Fisher), Water: re-distilled, and the rest was analytical pure.

3.2.3 Methods

Take 15 mg each of BC-SME 1 and BC-SME 2, add 10 ml of the methanol-methylene dichloride (9:1) mixture, dissolve with ultrasound and filter. Take 1 mg each of dihydrotanshinone, cryptotanshinone, tanshinone I and tanshinone IIA, add 2 ml of the methanol-methylene dichloride (9:1) mixture respectively for the mixed solution standards. Following the TLC method (Chinese Pharmacopoia 2005 Version Vol. I Appendix VI B) take 50 of each the test solutions, together with 3 µl each of the above-mentioned mixed solution standards, place them respectively on the same silica gel G plate, using petroleum ether-tetrahydrofuran-methanol (10:2:1) as the developing system, examine under the sunlight.

3.2.4 Results

Put the sample drops on the same silica gel G plate with the reference drops. The spots corresponding to the reference compounds showed the same color at the same positions. The TLC experiment was repeated three times.

The Results are shown in FIGS. 5a, 5b and 5c

In each:
Lane 1: SME-1,
Lane 2: SME-2 and
Lane: reference compounds. Reading bottom to top these are:
Dihydrotanshinone,
Cryptotanshinone,
Tanshinone I, and
Tanshinone IIA.

3.2.5 Discussion

From the experimental results under these chromatographic conditions, the separation of the mixed reference compounds and samples of the tanshinone compounds were very good, and the clear spots of the reference compounds could be seen in the samples of BC-SME 1 and BC-SME 2.

4.0 Improved Extraction—Comparison Between Thermal Reflux and Percolation

Tanshinone compounds are lipid-soluble, so a high concentration ethanol (95% ethanol) was used as an extraction medium. A comparison between reflux and percolation extraction was made with a view to determining if a commercially scalable process giving a higher yield rate of cryptotanshinone and reduced impurity could be attained.

4.1 Percolation Extraction

Soak 70 g of Danshen raw material in 95% ethanol for 12 hours and extract with 12 times its volume of 95% ethanol. The colature was collected and the ethanol recovered. The resulting extract was then dried with a vacuum concentrator and weighed. 40 mg of the dry solid extract was weighed and put it into a 50 ml volumeteric flask, dissolved with the mobile phase solution, diluted to volume, filtered and analysed with HPLC.

4.2 Reflux Methods

Reflux 70 g of Danshen raw material with 6 times its own volume of 95% ethanol twice, for 1.5 hours on each occasion. The ethanol was recovered and the extract dried with a vacuum concentrator and weighed. 40 mg of the dry solid extract was placed into a 50 ml volumeteric flask; dissolved with the mobile phase solution, filtered and analysed with HPLC.

4.3 Results

The Results showed that the extraction by using the percolation methods can raise the content and the conversion rate of cryptotanshinone but its yield rate was lower than that with the reflux methods.

The different percolation methods selected, the yield rates, and the content and conversion rates of the extracts produced by the two different methods are set out in Table 6 below.

TABLE 6

Selection of the cryptotanshinone extraction methods

| Methods | Yield Rate (%) | Content (mg/g extract) | Conversion Rate (%) |
|---|---|---|---|
| Percolation 1 | 4.96 | 84.53 | 95.29 |
| Percolation 2 | 4.77 | 87.41 | 94.76 |
| Reflux 1 | 9.28 | 39.25 | 82.78 |
| Reflux 2 | 9.44 | 40.00 | 85.82 |

From the results it can be seen that percolation results in a significantly greater content (on a mg/g of extract basis) than reflux. Furthermore it is advantageous in that it uses simple equipment, is safe to operate, and is energy efficient. The extraction at room temperature also reduces damage to the active components, which are heat and light sensitive, and easily degraded.

4.4 Optimization of Percolation Method

In order to optimize the process parameters of percolation extraction an orthogonal test was carried out and the conversion rate of cryptotanshinone used as an investigation indicator.

4.4.1. Design of Orthogonal Test

An orthogonal test was designed to determine what factors might influence the conversion rate of cryptotanshinone.

Three factors were selected for the orthogonal test:
(A) Solvent consumption,
(B) Soaking time, and
(C) Outflow velocity.

Three levels were selected for each factor.

The conversion rate of cryptotanshinone was selected as the investigation indicator; analysis was carried out by using direct-vision methods and analysis of variance (ANOVA).

The test was carried out as set out in Table 7.

TABLE 7

| Level | A Ethanol Consumption (folds) | B Soaking Time (h) | C Outflow Velocity (ml/min−1) |
|---|---|---|---|
| 1 | 10 | 6 | 10 |
| 2 | 12 | 12 | 15 |
| 3 | 14 | 24 | 20 |

4.4.2 Design Methodology

Measure 9 portions, 70 g each of the crude powder of Danshen raw material. Each portion was soaked respectively in an appropriate quantity of 95% ethanol for half an hour. Carry out the percolation under the conditions set out in Table 7. The respective solutions were collected and dried with vacuum concentration. The ethanol was recovered from each resulting solution and the extracts were dried under vacuum at 60° C., and weighed. 40 mg of dried extract was weighed into a 50 ml volumetric flask, dissolved into the mobile phase solution to volume, and filtered. The solutions were used for HPLC analysis.

4.4.3 Results of Orthogonal Test

From the analysis of variance (ANOVA), three factors affected the conversion rate of Cryptotanshinone; the 3 influence degrees were A>C>B. The optimization grouping was A2B3C2, that is, in the conditions of 95% ethanol of 12 folds its volume, soaking for 24 hours, outflow velocity: 15 ml/min The results are shown in Table 8.

TABLE 8

| Nos | A | B | C | D (Blank) | Conversion Rate of Cryptotanshinone (%) |
|---|---|---|---|---|---|
| 1 | 1 | 1 | 1 | 1 | 84.20 |
| 2 | 1 | 2 | 2 | 2 | 91.77 |
| 3 | 1 | 3 | 3 | 3 | 97.39 |
| 4 | 2 | 1 | 2 | 3 | 97.84 |
| 5 | 2 | 2 | 3 | 1 | 90.07 |
| 6 | 2 | 3 | 1 | 2 | 92.14 |
| 7 | 3 | 1 | 3 | 2 | 87.07 |
| 8 | 3 | 2 | 1 | 3 | 79.77 |
| 9 | 3 | 3 | 2 | 1 | 89.45 |
| K1 | 273.36 | 269.11 | 256.11 | 263.72 | $G = \Sigma Y_i = 809.70$ |
| K2 | 287.00 | 261.61 | 279.06 | 270.98 | $CT = G^2/9 = 72846.01$ |
| K3 | 256.29 | 278.98 | 274.53 | 275.00 | $Q = 1/3 \Sigma K^2_i$ |
| Q | 74259.75 | 72896.61 | 72944.51 | 72867.80 | $SS = Q-CT$ |
| SS | 1413.74 | 50.60 | 98.50 | 21.79 | |

| Source for ANOVA | SS | f | S | F |
|---|---|---|---|---|
| A | 1413.74 | 2 | 706.87 | 64.88 |
| B | 50.60 | 2 | 25.30 | 0.51 |
| C | 98.50 | 2 | 49.25 | 4.52 |
| Difference | 21.79 | 2 | 10.89 | |

4.4.4 Optimised Percolation Process

Based on the results of the orthogonal test, three validation tests were carried out for the optimized process. The results are illustrated in Table 9

TABLE 9

| Proof Tests | Yield Rate (%) | Content of Cryptotanshinone (mg/g extract) | Conversion Rate of Cryptotanshinone (%) |
|---|---|---|---|
| 1 | 4.82 | 86.98 | 95.28 |
| 2 | 4.85 | 86.06 | 94.86 |
| 3 | 4.84 | 86.30 | 94.93 |

5.0 Activity Enhancement Step

The applicant sought a methodology to selectively enhance the content of tanoshinone compounds in the extract and the methodology in this example demonstrates a process which, in the first instance increases the content of tanoshines approximately two fold but significantly increases the relative content of cryptanoshinone content by an even greater factor. This is particular advantageous from a pharmaceutical activity perspective.

5.1 Design of the Experiment

Improved Extraction/Purification Process

The process is illustrated in FIG. 6 and comprises the following steps:

1. Extract Danshen raw material with 95% ethanol with percolation and concentrate using vacuum drying;
2. Dissolve the extract with water;
3. Extract the solution with ethyl acetate; and
4. Purify with silica gel column;

5.1.1 Purification of Danshen Fractions

Danshen raw material: Batch No. DS0601.

Select 106.5 g of clean raw material and crush to a powder. Soak in an appropriate quantity of 95% ethanol for 24 hours, distribute it well into the percolator, and extract with percolation with a flow rate of 15 ml/min. Collect the colature of 12 times the raw material, i.e. 1280 ml. Recover the ethanol under vacuum. Vacuum dry at 70° C. to get the final extract, 10.2 g.

The final percolation extract of Danshen was given a batch number—SL0601.

5.1.2 Preparation of Ethyl Acetate Extract

Take the final extract of Danshen mentioned in 5.1.1 above, add 100 ml water and extract it with 150 ml ethyl acetate twice; combine the two ethyl acetate solutions and dehydrate. Wash it with 100 ml and 50 ml water respectively and dehydrate. Concentrate the ethyl acetate extract under vacuum to obtain 5.765 g of a solid extract which was given a batch number—YY0601.

5.1.3 Silica Gel Purification

Measure 2.0022 g of Danshen ethyl acetate extract (as 5.1.2), dissolve it with acetone, mix it fully with silica gel and remove the solvent. Apply the sample to a silica gel column, elute with petroleum ether-acetone in different proportions. Collect 50 ml eluate in each fraction The fractions collected are shown in Table 10 below:

TABLE 10

| Types of Eluate | Volume (ml) | Portions collected |
|---|---|---|
| petroleum ether - acetone (97:3) | 900 | 18 |
| petroleum ether - acetone (95:5) | 300 | 6 |
| petroleum ether - acetone (90:10) | 300 | 6 |

TABLE 10-continued

| Types of Eluate | Volume (ml) | Portions collected |
|---|---|---|
| petroleum ether - acetone (80:20) | 350 | 7 |
| petroleum ether - acetone (50:50) | 500 | 1 |
| methanol | 500 | 1 |

Each fraction was applied on silica gel TLC plates, and petroleum ether-acetone was used as the developing system. Examination was under natural sunlight. The TLC fingerprints are shown in FIG. 7

Based on the TLC result a number of consecutive fractions were merged as follows:
2nd and 3rd;
5th to 8th;
10th to 13th;
14th and 5th;
16th to 18th;
19th to 21st;
23rd and 24th;
25th and 26th;
28th to 30th;
31st to 34th;
35th and 36th.

The resulting 20 new fractions were analyzed with Silical gel TLC and the results are shown in FIG. 8.

The fractions showing the highest contents of cryptotanshinone and dihydrotanshinone, i.e. the 7th to the 13th samples, were combined as "purified tanshinones" (0.420 g). This purified tanshinone containing compound extract was given a batch number: JZ0601.

The ethyl acetate extract of Danshen (Lane 1), the purified tanshinones (Lane 2) and the mixed tanshinone standards were examined with silica gel TLC. The TLC fingerprint is shown in FIG. 9. The compounds from bottom to top are respectively:
Dihydrotanshinone,
Cryptotanshinone,
Tanshinone I, and
Tanshinone IIA The chromatographic conditions were as described in 3.1.3 above (Table 3 gradient 1).

5.1.4 Samples

The samples obtained at the three stages, namely:
Danshen percolation extract, SL0601,
Danshen ethyl acetate extract, YY0601, and
Purified tanshinones, JZ0601, were additionally subjected to HPLC chromatographic analysis as described in 3.1.

5.1.5 Method and Analysis

Weigh accurately:
Danshen percolation extract 50.8 mg,
Danshen ethyl acetate extract 19.3 mg and
Purified tanshinones 11.9 mg, Put them into a 10 ml volumetric flask respectively; add 8 ml of the methanol-methylene dichloride (9:1) solution, dissolve with ultrasonication, add the methanol-methylene dichloride (9:1) solution to volume, shake thoroughly and filter. Carry out HPLC analysis. The resulting HPLC fingerprints are shown in FIGS. 10a to 10d.:

FIG. 10a is an HPLC chromatogram of a percolation extract under conditions as set out in Table 3 (gradient 1) (SL0601);

FIG. 10b is an HPLC chromatogram of a ethyl acetate purified extract under conditions as set out in Table 3 (gradient 1) (YY0601);

FIG. 10c is an HPLC chromatogram of a silica gel purified extract under conditions as set out in Table 3 (gradient 1) (JZ0601); and the comparator FIG. 10d is an HPLC chromatogram of reference compounds under conditions as set out in Table 3 (gradient 1).

The content of each compound from HPLC analysis is shown in Table 11.

TABLE 11

| Samples Peak Names | Danshen Percolation Extract (%) Content | Ethyl Acetate Extract (%) | | Purified Tanshinones (%) | |
|---|---|---|---|---|---|
| | | Content | Conversion Rate | Content | Conversion Rate |
| Dihydrotanshinone | 1.59 | 2.64 | 93.65 | 4.96 | 39.45 |
| Tanshinone I | 2.04 | 3.57 | 98.97 | 5.34 | 31.35 |
| Cryptotanshinone | 4.23 | 6.46 | 86.41 | 30.18 | 97.96 |
| Tanshinone IIA | 7.49 | 13.39 | 100.97 | 8.57 | 13.44 |
| Total: | 15.35 | 26.06 | | 49.06 | |
| Inventory (g) | 106.50 | 10.20 | | 2.00 | |
| Yield (g) | 10.20 | 5.77 | | 0.42 | |
| Yield Rate (%) | 9.58 | 56.57 | | 21.00 | |

The content of the four identified tanshinones in the purified tanshinone extract was 49.06% and the content of cryptotanshinone was 30% as the dominant component.

Silica Gel Column Chromatography was demonstrated to be an effective method for purifying cryptotanshinone. The content of cryptotanshinone rose significantly to eliminate the non-active compounds from the ethyl acetate extraction. This purified tanshinones fraction was further studied for its antibacterial activity.

5.1.6 Activity

Samples: purified Tanshinones, Batch No. JZ0601,
Test Lab: National Institute for the Control of Pharmaceutical and Biological Products (NICPBP), National Center for Drug Resistance of Bacteria Beijing, PR China.

The testing solution was prepared as follows:
1. Place 6.40 mg of the sample into a 50 ml volumetric flask and add 15 ml DMF solution (N,N-Dimethylformamide)
2. Ultrasonicate for 10 minutes.
3. Add 15 ml of water to dilute the solution and ultrasonicate immediately for 5 minutes.

4. Add water to the volume and shake well, then ultrasonicate for another 5 minutes to obtain the testing solution of 0.128 mg/ml (30% DMF concentration).

Bacterial Strains:

107 strains collected and kept by National Monitoring Center for Antibiotic Resistant Bacterial (China) were used to test the activity. The strains were evaluated with the Phoenix-100 automated Microbiology System. The testing strains included:

- 87 strains of *Staphylococcus aureus* (SA) including 52 strains of methicillin resistant SA (MRSA) and 35 strains of methicillin susceptible SA (MSSA);
- 23 strains of Coagulase-negative Staphylococci (CNS) (MRCNS 4 and MSCNS19); and
- 7 strains of *Streptococcus* (5 strains of *Streptococcus pneumoniae*).

Drug Susceptibility Test:

A microtitre broth dilution method (MH Broth, Oxoid Ltd UK) was used in the testing. The minimum inhibitory concentrations (MICs) of flucloxacillin/ampicillin on the isolated strains were tested based on the methods described on America CLSI/NCCLS Antimicrobial Susceptibility Testing (AST) (2006)

Bacterial strains used for quality control:
*Staphylococcus aureus*, (ATCC 29213) and
*Streptococcus pneumoniae* (ATCC49619).

Statistical Analysis:

WHONET software (version 5.3) supplied by WHO.

Results:

1. The MIC of penicillin against *Staphylococcus aureus*, (ATCC 29213) and *Streptococcus Pneumoniae* (ATCC49619) were conformed to CLSI/NCCLS (2006).

2. The MICs of JZ0601 against *Staphylococcus* and *Streptococcus* were as set out in Tables 12.

TABLE 12

| Strains | Testing Nos. | MIC50 (µg/ml) | MIC90 (µg/ml) | MIC (µg/ml) Range |
|---|---|---|---|---|
| SA | 87 | 8 | 16 | 0.25-16 |
| MSSA | 35 | 8 | 16 | 0.25-16 |
| MRSA | 52 | 8 | 16 | 4-16 |
| CNS | 23 | 8 | 16 | 2-16 |
| *Streptococcus* | 7 | 16 | 16 | 16 |

Summary

JZ0601 showed good activity against *Staphylococcus* including methicillin susceptible and resistant strains, as well as *Streptococcus*, particularly *Streptococcus pneumoniae*. The MICs of JZ0601 on all strains are as set out in Tables 13-16:

TABLE 13

MICs of JZ0601 on 35 strains of methicillin susceptible *Staphylococcus aureus*

| serial number | Strain code | MIC (µg/ml) |
|---|---|---|
| 1 | sau865 | 8 |
| 2 | guangzongsau | 8 |
| 3 | Guangzongsau-2 | 8 |
| 4 | tjsau62 | 4 |
| 5 | tjsau52 | 2 |
| 6 | sau511524 | 8 |
| 7 | sau511837 | 8 |
| 8 | saubeisan50 | 8 |
| 9 | a838 | >8 |

TABLE 13-continued

MICs of JZ0601 on 35 strains of methicillin susceptible *Staphylococcus aureus*

| serial number | Strain code | MIC (µg/ml) |
|---|---|---|
| 10 | sau839 | >8 |
| 11 | mssa17 | 8 |
| 12 | a10 | >8 |
| 13 | a104 | 8 |
| 14 | sau59 | 8 |
| 15 | a85 | 4 |
| 16 | abeisan29 | 4 |
| 17 | ayou130 | 0.25 |
| 18 | mssa10 | 8 |
| 19 | mssa20 | >8 |
| 20 | mssa16 | 8 |
| 21 | saubeisan44 | 2 |
| 22 | mssa2 | 8 |
| 23 | mssa201 | 8 |
| 24 | mssa25 | 8 |
| 25 | mssa2949 | 8 |
| 26 | mssa8 | 8 |
| 27 | mssa855 | 4 |
| 28 | tjsau53 | 0.25 |
| 29 | saubeisan44 | 2 |
| 30 | tjsau52 | 2 |
| 31 | saubeisan45 | 8 |
| 32 | tjsau59 | 8 |
| 33 | tjsau60 | >8 |
| 34 | tjsau69 | 4 |
| 35 | ayou196 | 8 |

TABLE 14

MICs of JZ0601 on 52 strains of methicillin resistant *Staphylococcus Aureus*

| serial number | Strain code | MIC (µg/ml) |
|---|---|---|
| 1 | gdmrsa9103 | 4 |
| 2 | mrsa18 | 8 |
| 3 | beisanmrsa16 | 4 |
| 4 | beisanmrsa21 | 8 |
| 5 | mrsa15 | 8 |
| 6 | mu3* | 8 |
| 7 | mu50* | 4 |
| 8 | mrsa420 | 8 |
| 9 | mrsa13 | 8 |
| 10 | mrsa19 | 8 |
| 11 | mrsa2 | 4 |
| 12 | 511400 | 4 |
| 13 | mrsa3409 | 8 |
| 14 | mrsa3479 | 8 |
| 15 | zjmrsa619057 | >8 |
| 16 | mrsa5002 | 8 |
| 17 | gdmrsa69 | 4 |
| 18 | mrsa5120 | 8 |
| 19 | mrsa60578 | 8 |
| 20 | wuhao | 8 |
| 21 | mrsa5153 | 8 |
| 22 | zjmrsa614036 | 8 |
| 23 | zjmrsa614036 | 8 |
| 24 | zjmrsa613066 | >8 |
| 25 | zjmrsa612011 | >8 |
| 26 | zjmrsa708015 | >8 |
| 27 | zjmrsa705013 | 4 |
| 28 | zjmrsa611049 | 8 |
| 29 | zjmrsa709037 | >8 |
| 30 | zjmrsa611045 | 8 |
| 31 | mrsa40452 | 4 |
| 32 | gxmrsa7497 | 8 |
| 33 | zjmrsa160578 | 4 |
| 34 | zjmrsa607022 | 4 |
| 35 | zjmrsa608007 | >8 |
| 36 | gxmrsa7402 | 8 |

TABLE 14-continued

MICs of JZ0601on 52 strains of methicillin resistant Staphylococcus Aureus

| serial number | Strain code | MIC (µg/ml) |
|---|---|---|
| 37 | mrsa516484 | 4 |
| 38 | mrsa516467 | 8 |
| 39 | mrsa516390 | 4 |
| 40 | gxmrsa3536 | 8 |
| 41 | gxmrsa4221 | 8 |
| 42 | gxmrsa5450 | 8 |
| 43 | zjmrsa809078 | >8 |
| 44 | gxmrsa7345 | >8 |
| 45 | mrsa127007 | 8 |
| 46 | gdmrsa12 | 8 |
| 47 | zjmrsa731066 | 8 |
| 48 | zjmrsa723053 | 8 |
| 49 | zjmrsa723017 | >8 |
| 50 | zjmrsa711067 | 8 |
| 51 | zjmrsa710008 | 8 |
| 52 | gxmrsa6372 | 8 |

Note:
*vancocin intermediary Staphylococcus Aureus

TABLE 15

MICs of JZ0601on 23 strains of Coagulase-negative Staphylococci

| serial number | Strain code | MIC (µg/ml) |
|---|---|---|
| 1 | sep207481 | 8 |
| 2 | sep786 | 8 |
| 3 | sep207357 | 8 |
| 4 | who6 | 8 |
| 5 | sep999 | 8 |
| 6 | sep339 | 4 |
| 7 | 209166 | >8 |
| 8 | sep207518 | 8 |
| 9 | sep474 | 8 |
| 10 | sep207742 | >8 |
| 11 | sep212419 | 2 |
| 12 | 104023 | 4 |
| 13 | 105510 | >8 |
| 14 | sep154 | 8 |
| 15 | 537244 | 8 |
| 16 | 212229 | 2 |
| 17 | 212158 | 2 |
| 18 | SEP154-2 | 8 |
| 19 | 1559 | >8 |
| 20 | Zhongshanyi# | >8 |
| 21 | mrse511453# | 8 |
| 22 | mrse36915# | 8 |
| 23 | msse79647# | 8 |

Note:
methicillin resistant CNS

TABLE 16

MICs of JZ0601 on 7 strains of Streptococcus

| serial number | Strain code | MIC (µg/ml) |
|---|---|---|
| 1 | spy19615 | 16 |
| 2 | *spnA534 | 16 |
| 3 | *spn724 | 16 |
| 4 | *spn6305 | 16 |
| 5 | *spn16732 | 16 |
| 6 | *hb733-15 | 16 |
| 7 | sag13813 | 16 |

Note:
*Streptococcus pneumoniae.

The above data demonstrates the benefits of using an extract which is not only characterized by its high tanoshinone compounds content but more particularly one with enhanced levels of particularly cryptotanoshinone.

However, the methodology described to obtain this highly purified extract was not suitable for scale up and accordingly an alternative scalable methodology had to be developed. This is described below:

6.0 Scalable Methodology

The preferred commercial scale production process for obtaining a selectively purified tanshinone compounds containing extract from the root of Salvia Spp, and more particularly one specifically enriched in cryptotanshinone, is set out with reference to FIG. 11

6.1 General Methodology

1. Take Danshen raw material;
2. Soak it with a sufficient volume of high concentration, typically 95%, ethanol for a time sufficient to solubilise the desired compounds, typically 24 hours;
3. Place the material into a percolator and extract using a percolation method;
4. Collect the ethanol solution with, typically, 12 times volume of its raw material at the desired percolation speed, preferably, 15 ml·min-1;
5. Concentrate the liquid extract under vacuum and recover the ethanol to obtain the ethanol extract.

The yield rate is about 5-9%.
The content of the total tanshinones is about 8%.

6.2 Purification

1. Dissolve the ethanol extract with about 10 times of water,
2. Dispose of the aqueous solution and collect the precipitate.

The yield rate is about 40% and the content of the total tanshinones is about 20%.

3. Dissolve the precipitates with 60% ethanol and place the material onto an AB-8 macroporous resin column.
4. Elute with 60% ethanol and dispose of the fraction
5. Elute with 70% ethanol to obtain the selectively purified fraction containing tanshinones.

The yield rate is 16-22%
The content of the total tanshinones is up to 40%.

6.3 Specification

The resulting purified extract has a specification as set out in Table 17

TABLE 17

| ITEMS | SPECIFICATION |
|---|---|
| Appearance | Redish-brown colour |
| Source | Purified extract made from the dry root and rhizome of Salvia miltiorrhiza Bge. (Labiatae family) |
| Chemical Constituents | Total Tanshinones ≥40% (including Dihydrotanshinone, Cryptotanshinone, Tanshinone I and Tanshinone IIA) |
| Identification | (1) TLC Identification corresponds to the standard chromatography<br>(2) HPLC Identification corresponds to the standard chromatography |
| Inspection | (1) Moisture <5.0%<br>(2) Total Ash <5.0%<br>(3) Acid Insoluble Ash <2.0%<br>(4) Heavy Metals <10 ppm<br>(5) Arsenic <2 ppm |

TABLE 17-continued

| ITEMS | SPECIFICATION | |
|---|---|---|
| Microbial Detection | (1) Total Plate Count | <1000 cfu/g |
| | (2) Fungal&Yeast | <100 cfu/g |
| | (3) *E. coli* | Neg. |
| | (4) *Salmonelia* | Neg. |
| Storage | Store in a cool, dry place and avoid sunlight | |

The extract can be identified chromatographically be either TLC or HPLC as set out below:

6.4 TLC
Preparation of the Standard Reference Solution
1. Take 1 mg each of:
Dihydrotanshinone,
Cryptotanshinone,
Tanshinone I, and
Tanshinone IIA
standard reference chemicals
2. Add 2 ml of a mixed solution of methanol-methylene dichloride (9:1) to dissolve the substances to obtain the mixed standard reference solution.
Preparation of the Test Solution
1. Weigh 15 mg of JZ0702 (extract as FIG. 11),
2. Add 10 ml of the mixed solution of methanol-methylene dichloride (9:1) and dissolve the sample by ultrasonication to obtain the test solution.
Detection Method
According to the TLC method described in the Chinese Pharmacopoeia 2005 Version, Vol. 1, Appendix VI B,
1. Place 5 μl of above-mentioned test solution and 3 μl of the mixed standard solution onto a silica G plate,
2. Develop the plate with petroleum a mixed solvent: ether-tetrahydrofuran-methanol (10:2:1).
3. Dry the plate after development and observed the plate under daylight.

The test sample showed colour spots in the position corresponding to that of the reference chemicals in the chromatogram (FIG. 12).

The TLC methodology is qualitative rather than quantitative.

6.5 HPLC
Chromatographic Conditions
As section 3.1.3. Table 4 (gradient 2)
Preparation of Reference Solution
Weigh accurately 1 mg each of:
Dihydrotanshinone,
Cryptotanshine, and
Tanshinone 1
and 2 mg of:
Tanshinone IIA
Place them into a 10 ml volumetric flask, add 8 ml of the mixed solvent of methanol-methylene dichloride (9:1) and ultrasonicate for 5 min.
Add the mixed solvent to the volume and shake thoroughly to obtain the reference solution.
Preparation of Sample Solutions
1. Weigh accurately 10 mg of JZ0702 and put it into a 10 ml volumetric flask.
2. Add 8 ml of mixed solvent methanol-methylene dichloride (9:1) and ultrasonicate for 5 min.
3. Add the mixed solvent to the volume and shake fully to obtain the test solution.
Assay Method
Inject 5 μl each of both the test solution and the reference solution respectively into an HPLC column and run. The profile for the extract is illustrated in FIG. 13 and compared to the reference sample FIG. 14

From this the four tanshinones were calculated to be 42.89% of the extract, calculated as:
Dihydrotanshinone (3.65%),
Cryptotanshinone (18.95%),
Tanshinone I (3.82%), and
Tanshinone IIA (16.47%)

7.0 Activity Against *Propionibacterium acnes*

Objective:
To evaluate the in vitro activity of a selectively purified tanshinone compounds containing extract against the anaerobic bacteria *Propionibacterium acnes* (*P. acnes*).

Methods:
A selectively purified tanshinone compounds containing extract was added to wells containing *P. acnes* (ATCC 6919; $1 \times 10^4$ to $5 \times 10^5$ CFU/mL) in culture, grown under controlled conditions (reinforced clostridial medium, 37° C.). Final inoculum concentration was determined by reference to a standard optical density curve and adjusted as necessary. Wells were incubated for 48 hours at 37° C. and examined for growth of culture. Wells were scored positive (+) for inhibition of growth, or negative (−) for no effect on growth. Eight different concentrations ranging from 0.03 μg/mL-100 μg/mL were screened. Ampicillin was run at a concentration of 0.1 μg/mL as a positive control. MIC and MBC were calculated.

Results:
The extract was tested at half-log concentrations of 0.03 μg/mL to 100 μg/mL for potential bactericidal activity against *P. acnes*. From this, a minimum inhibitory concentration (MIC) of 10 μg/mL was determined, and a minimum bactericidal concentration (MBC) of 30 μg/mL was calculated. The results are shown in Table 18.

TABLE 18

Microbial analysis scoring of PYN6's inhibitory affect on *P. acnes*

| Concentration | Growth inhibition (MIC) | Growth inhibition (MBC) |
|---|---|---|
| 0.03 μg/mL | − | − |
| 0.1 μg/mL | − | − |
| 0.3 μg/mL | − | − |
| 1 μg/mL | − | − |
| 3 μg/mL | − | − |
| 10 μg/mL | + | − |
| 30 μg/mL | + | + |
| 100 μg/mL | + | + |

(− = no inhibition; + = inhibition).

Conclusion
The extract showed antibiotic activity against *P. acnes* with a MIC of 10 μg/mL (MBC of 30 μg/mL).

8.0 Experiment to Determine Potential for Resistance Development

This experiment was conducted to test for the rapid development of resistance in *Staphylococcus aureus* in the presence of sub-inhibitory doses of the active extract.

Materials and Methods
Bacterial Strains
Oxford *Staphylococcus aureus* (NCTC 6571) and 3 clinical isolates of MRSA were tested, T3, 102 and MRSA 99. All clinical strains were from The Royal London, St Bartholomew's or Newham hospitals in London. Each strain had been identified as an MRSA.

Active Extract/Ciprofloxacin/Gentamicin
Active extract powder (Phynova)
Ciprofloxacin (Bayer Pharmaceutical)
Gentamicin powder (Sigma chemicals)
Solubilisation of PYN6
The standard method using DMF was used. Manufacturer's method using DMF where the solution was unfiltered prior to use. Solution—640 mg/l was added to 3 ml DMF, sonicated in a sonic water bath then made up to 10 ml with water as per instructions.

Development of Resistance Testing

High concentrations of organisms ($10^7 cfu/ml^{-1}$) were grown in sub-inhibitory concentrations 0, 2 and 8 mg $l^{-1}$ of the active extract. MICs had been determined previously as 16 mg $l^{-1}$.

Organisms were sub-cultured into fresh active extract media at day 4 and again at day 7. MICs were checked weekly using standard methods. Subcultures were carried out in triplicate.

Results

No change in MIC was observed over the 3 week test period. No growth indicates the MIC level. Three MRSA clinical isolates have been tested and control Strain Oxford *Staphylococcus aureus* Tables 19, 20, 21 and 22. Table 23 shows the comparative development of resistance with Ciprofloxicin and table 24 for gentamicin.

There was no development of resistance for the active extract or gentamicin. The MICs to ciprofloxacin increased after 2 weeks treatment.

TABLE 19

Subculture results showing MIC after extended culture at sub-inhibitory doses for MRSA T3

| Day | Sub culture concentration mg $l^{-1}$ | Organism | Growth Control | Growth 2 mg $l^{-1}$ | Growth 8 mg $l^{-1}$ | Growth 16 mg $l^{-1}$ | Growth 32 mg $l^{-1}$ |
|---|---|---|---|---|---|---|---|
| 1 | 0 | T3 | + | + | + | − | − |
| 1 | 0 | T3 | + | + | + | − | − |
| 1 | 4 | T3 | + | + | + | − | − |
| 1 | 4 | T3 | + | + | + | − | − |
| 1 | 8 | T3 | + | + | + | − | − |
| 1 | 8 | T3 | + | + | + | − | − |
| 7 | 0 | T3 | + | + | + | − | − |
| 7 | 0 | T3 | + | + | + | − | − |
| 7 | 4 | T3 | + | + | + | − | − |
| 7 | 4 | T3 | + | + | + | − | − |
| 7 | 8 | T3 | + | + | + | − | − |
| 7 | 8 | T3 | + | + | + | − | − |
| 14 | 0 | T3 | + | + | + | − | − |
| 14 | 0 | T3 | + | + | + | − | − |
| 14 | 4 | T3 | + | + | + | − | − |
| 14 | 4 | T3 | + | + | + | − | − |
| 14 | 8 | T3 | + | + | + | − | − |
| 14 | 8 | T3 | + | + | + | − | − |
| 21 | 0 | T3 | + | + | + | − | − |
| 21 | 0 | T3 | + | + | + | − | − |
| 21 | 4 | T3 | + | + | + | − | − |
| 21 | 4 | T3 | + | + | + | − | − |
| 21 | 8 | T3 | + | + | + | − | − |
| 21 | 8 | T3 | + | + | + | − | − |

TABLE 20

Subculture results showing MIC after extended culture at sub-inhibitory doses for MRSA 99

| Day | Sub culture concentration mg $l^{-1}$ | Organism | Growth Control | Growth 2 mg $l^{-1}$ | Growth 8 mg $l^{-1}$ | Growth 16 mg $l^{-1}$ | Growth 32 mg $l^{-1}$ |
|---|---|---|---|---|---|---|---|
| 1 | 0 | 99 | + | + | + | − | − |
| 1 | 0 | 99 | + | + | + | − | − |
| 1 | 4 | 99 | + | + | + | − | − |
| 1 | 4 | 99 | + | + | + | − | − |
| 1 | 8 | 99 | + | + | + | − | − |
| 1 | 8 | 99 | + | + | + | − | − |
| 7 | 0 | 99 | + | + | + | − | − |
| 7 | 0 | 99 | + | + | + | − | − |
| 7 | 4 | 99 | + | + | + | − | − |
| 7 | 4 | 99 | + | + | + | − | − |
| 7 | 8 | 99 | + | + | + | − | − |
| 7 | 8 | 99 | + | + | + | − | − |
| 14 | 0 | 99 | + | + | + | − | − |
| 14 | 0 | 99 | + | + | + | − | − |
| 14 | 4 | 99 | + | + | + | − | − |
| 14 | 4 | 99 | + | + | + | − | − |
| 14 | 8 | 99 | + | + | + | − | − |
| 14 | 8 | 99 | + | + | + | − | − |

TABLE 20-continued

Subculture results showing MIC after extended
culture at sub-inhibitory doses for MRSA 99

| Day | Sub culture con-centration mg l$^{-1}$ | Organism | Growth Control | Growth 2 mg l$^{-1}$ | Growth 8 mg l$^{-1}$ | Growth 16 mg l$^{-1}$ | Growth 32 mg l$^{-1}$ |
|---|---|---|---|---|---|---|---|
| 21 | 0 | 99 | + | + | + | − | − |
| 21 | 4 | 99 | + | + | + | − | − |
| 21 | 4 | 99 | + | + | + | − | − |
| 21 | 8 | 99 | + | + | + | − | − |
| 21 | 8 | 99 | + | + | + | − | − |

TABLE 21

Subculture results showing MIC after extended
culture at sub-inhibitory doses for MRSA 99

| Day | Sub culture con-centration mg l$^{-1}$ | Organism | Growth Control | Growth 2 mg l$^{-1}$ | Growth 8 mg l$^{-1}$ | Growth 16 mg l$^{-1}$ | Growth 32 mg l$^{-1}$ |
|---|---|---|---|---|---|---|---|
| 1 | 0 | 102 | + | + | + | − | − |
| 1 | 0 | 102 | + | + | + | − | − |
| 1 | 4 | 102 | + | + | + | − | − |
| 1 | 4 | 102 | + | + | + | − | − |
| 1 | 8 | 102 | + | + | + | − | − |
| 1 | 8 | 102 | + | + | + | − | − |
| 7 | 0 | 102 | + | + | + | − | − |
| 7 | 0 | 102 | + | + | + | − | − |
| 7 | 4 | 102 | + | + | + | − | − |
| 7 | 4 | 102 | + | + | + | − | − |
| 7 | 8 | 102 | + | + | + | − | − |
| 7 | 8 | 102 | + | + | + | − | − |
| 14 | 0 | 102 | + | + | + | − | − |
| 14 | 0 | 102 | + | + | + | − | − |
| 14 | 4 | 102 | + | + | + | − | − |
| 14 | 4 | 102 | + | + | + | − | − |
| 14 | 8 | 102 | + | + | + | − | − |
| 14 | 8 | 102 | + | + | + | − | − |
| 21 | 0 | 102 | + | + | + | − | − |
| 21 | 0 | 102 | + | + | + | − | − |
| 21 | 4 | 102 | + | + | + | − | − |
| 21 | 4 | 102 | + | + | + | − | − |
| 21 | 8 | 102 | + | + | + | − | − |
| 21 | 8 | 102 | + | + | + | − | − |

TABLE 22

Subculture results showing MIC after extended culture
at sub-inhibitory doses for Oxford *Staph aureus*.

| Day | Sub culture con-centration mg l$^{-1}$ | Organism | Growth Control | Growth 2 mg l$^{-1}$ | Growth 8 mg l$^{-1}$ | Growth 16 mg l$^{-1}$ | Growth 32 mg l$^{-1}$ |
|---|---|---|---|---|---|---|---|
| 1 | 0 | OX | + | + | + | − | − |
| 1 | 0 | OX | + | + | + | − | − |
| 1 | 4 | OX | + | + | + | − | − |
| 1 | 4 | OX | + | + | + | − | − |
| 1 | 8 | OX | + | + | + | − | − |
| 1 | 8 | OX | + | + | + | − | − |
| 7 | 0 | OX | + | + | + | − | − |
| 7 | 0 | OX | + | + | + | − | − |
| 7 | 4 | OX | + | + | + | − | − |
| 7 | 4 | OX | + | + | + | − | − |
| 7 | 8 | OX | + | + | + | − | − |
| 7 | 8 | OX | + | + | + | − | − |
| 14 | 0 | OX | + | + | + | − | − |
| 14 | 0 | OX | + | + | + | − | − |
| 14 | 4 | OX | + | + | + | − | − |
| 14 | 4 | OX | + | + | + | − | − |
| 14 | 8 | OX | + | + | + | − | − |
| 14 | 8 | OX | + | + | + | − | − |

TABLE 22-continued

Subculture results showing MIC after extended culture at sub-inhibitory doses for Oxford *Staph aureus*.

| Day | Sub culture concentration mg l$^{-1}$ | Organism | Growth Control | Growth 2 mg l$^{-1}$ | Growth 8 mg l$^{-1}$ | Growth 16 mg l$^{-1}$ | Growth 32 mg l$^{-1}$ |
|---|---|---|---|---|---|---|---|
| 21 | 0 | OX | + | + | + | − | − |
| 21 | 0 | OX | + | + | + | − | − |
| 21 | 4 | OX | + | + | + | − | − |
| 21 | 4 | OX | + | + | + | − | − |
| 21 | 8 | OX | + | + | + | − | − |
| 21 | 8 | OX | + | + | + | − | − |

TABLE 23

Subculture results showing MIC after extended culture at sub-inhibitory doses of Ciprofloxacin for MRSA T3 (MIC 0.5 mg l$^{-1}$)

| Day | Sub culture concentration mg l$^{-1}$ | Organism | Growth Control | Growth 8 mg l$^{-1}$ |
|---|---|---|---|---|
| 1 | 0 | T3 | + | − |
| 1 | 0 | T3 | + | − |
| 1 | 0.06 | T3 | + | − |
| 1 | 0.06 | T3 | + | − |
| 7 | 0 | T3 | + | − |
| 7 | 0 | T3 | + | − |
| 7 | 0.06 | T3 | + | − |
| 7 | 0.06 | T3 | + | − |
| 14 | 0 | T3 | + | − |
| 14 | 0 | T3 | + | − |
| 14 | 0.06 | T3 | + | + |
| 14 | 0.06 | T3 | + | + |
| 21 | 0 | T3 | + | − |
| 21 | 0 | T3 | + | − |
| 21 | 0.06 | T3 | + | + |
| 21 | 0.06 | T3 | + | + |

TABLE 24

Subculture results showing MIC after extended culture at sub-inhibitory doses of Gentamicin for MRSA T3 (MIC 4 mg l$^{-1}$)

| Day | Sub culture concentration mg l$^{-1}$ | Organism | Growth Control | Growth 8 mg l$^{-1}$ |
|---|---|---|---|---|
| 1 | 0 | T3 | + | − |
| 1 | 0 | T3 | + | − |
| 1 | 1 | T3 | + | − |
| 1 | 1 | T3 | + | − |
| 7 | 0 | T3 | + | − |
| 7 | 0 | T3 | + | − |
| 7 | 1 | T3 | + | − |
| 7 | 1 | T3 | + | − |
| 14 | 0 | T3 | + | − |
| 14 | 0 | T3 | + | − |
| 14 | 1 | T3 | + | − |
| 14 | 1 | T3 | + | − |
| 21 | 0 | T3 | + | − |
| 21 | 0 | T3 | + | − |
| 21 | 1 | T3 | + | − |
| 21 | 1 | T3 | + | − |

Conclusions

The extract is active against MRSA at inhibitory levels of 16 mg l$^{-1}$ and above. There was no change in the MIC level over the test period for the strains tested. No rapid development of resistance occurred and the test period was beyond that used by Boos M. et al. (In Vitro Development of Resistance to Six Quinolones in *Streptococcus pneumoniae, Streptococcus pyogenes*, and *Staphylococcus aureus. Antimicrob. Agents Chemother.* 45, 938-942) to demonstrate a seven fold increase in resistance to quinilones within 10 days.

9.0 Experiment to Determine Activity of PYN 6 in a Gel Formulation

A number of different gel formulations containing extracts of the invention were prepared and tested on clinical MRSA isolates to determine the suitability of the active extract for topical delivery.

10 clinical isolates of MRSA were tested.

Agar diffusion tests (based on BSAC standard methods) were used to compare the relative activity of different gels against MRSA. Zones of inhibition around each 100 ul sample were compared. PYN6 was prepared by dissolving in DMF and then water, final concentration 500 mg/L.

Results

FIG. 15 illustrates graphically of the effect of PYN6 in water and in gel formulations against 10 different strains of MRSA Gel 1 and 1(2)—Faith in Nature gels (glycerin based)

Gel6QM—QM thin gel (Proprietary-colloidal detergent based)

Gel1MQM—QM medium gel (Proprietary-colloidal detergent based)

Gel1FQM—QM full gel (Proprietary-colloidal detergent based)

Conclusions

All gels showed activity at a level of 500 mg/L. All were comparable to the activity of 500 mg/L PYN6 in water. PYN6 works in gel or water formulation and has potential as a topical antimicrobial against MRSA.

10.0 Experiment to Determine Activity of PYN 6 Against Individual Compounds

Methods

Minimum Inhibitory and Minimum Bactericidal activities (MIC and MBC) of PYN6 were determined for 2 strains of MRSA using standard microtitre well methods. MICs were determined by measuring growth over 20 hrs using spectroscopy at 490 nm. MBCs were determined by subculture from these microtitre plates onto solid media after 20 hrs and determining survival of bacteria grown in the presence of PYN6.

PYN6 Compounds

| Code | PYN6 compound |
|---|---|
| A | Tashinone 1 |
| B | Tashinone 11A |
| C | Dyhydrotashinone |

-continued

| Code | PYN6 compound |
|---|---|
| D | Cryptotashinone |
| PYN6 | PYN6 |

Results

TEST 1 MIC and MBC comparing PYN6 to A, B, C and D against MRSA 98

| Code | PYN6 compound | MIC mg/L | MBC mg/L |
|---|---|---|---|
| A | Tashinone 1 | 125 | <500 |
| B | Tashinone 11A | 125 | <500 |
| C | Dyhydrotashinone | 8 | 125 |
| D | Cryptotashinone | 15 | 250 |
| PYN6 | PYN6 | 31 | 125 |

TEST 2 MIC and MBC comparing PYN6 to A, B, C and D against MRSA 2

| Code | PYN6 compound | MIC mg/L | MBC mg/L |
|---|---|---|---|
| A | Tashinone 1 | 125 | >500 |
| B | Tashinone 11A | 125 | >500 |
| C | Dyhydrotashinone | 1.8 | 62 |
| D | Cryptotashinone | 7.7 | 125 |
| PYN6 | PYN6 | 7.7 | 125 |

The results demonstrate that PYN 6 an extract enriched in Cryptotashinone and Dyhydrotashinone (compared to Tashinone I and IIA-Table 5) performed very effectively.

The invention claimed is:

1. A topical gel formulation having antibacterial activity comprising a selectively purified extract from the root of a *Salvia* spp comprising the identified tanshinone compounds
   Cryptotashinone,
   Dihydrotanshinone,
   Tanshinone I, and
   Tanshinone IIA,
   said extract characterized in that the extract has antibacterial activity at a level of 16 micrograms per milliliter or less in the gel formulation and the identified tanshinone compounds comprise at least 35% by weight of the selectively purified extract; the cryptotanshinone is the dominant tanshinone compound and comprises at least 15% by weight of the selectively purified extract and at least 40% by weight of the total identified tanshinone compounds; the tanshinone IIA comprises less than 50% by weight of the total identified tanshinone compounds; and said extract has antibacterial activity against at least one drug resistant bacterium.

2. A topical gel formulation comprising the extract as claimed in claim 1 characterized in that the identified tanshinone compounds comprise at least 45%, by weight, of the total extract and the cryptotanshinone comprises at least 25%, by weight, of the selectively purified extract.

3. A topical gel formulation comprising the extract as claimed in claim 2 wherein the cryptotanshinone comprises at least 30% of the identified tanshinone compounds.

4. A topical gel formulation comprising the extract as claimed in claim 1 wherein the cryptotanshinone comprises at least 60% of the total identified tanshinone compounds.

5. A topical gel formulation comprising the extract as claimed in claim 1 wherein the tanshinone IIA comprises less than 45% of the identified tanshinone compounds.

6. A topical gel formulation comprising the extract as claimed in claim 5 wherein the tanshinone IIA comprises less than 40% of the identified tanshinone compounds.

7. A topical gel formulation comprising the extract as claimed in claim 6 wherein the tanshinone IIA comprises less than 20% of the identified tanshinone compounds.

8. A topical gel formulation comprising the extract as claimed in claim 1 characterized in that the extract comprises 34.31 to 51.47% by weight of the identified tanshinone compounds and has:
   a cryptotanshinone content of 15.16 to 22.74% by weight,
   a dihydrotanshinone content of 2.92 to 4.38% by weight,
   a tanshinone I content of 3.06 to 4.58% by weight, and
   a tanshinone IIA content of 13.18 to 19.76% by weight, all percentages by weight based on the total weight of the extract.

9. A topical gel formulation comprising the extract as claimed in claim 1 characterized in that the extract has an HPLC fingerprint substantially as illustrated in FIG. 13.

10. A topical gel formulation as claimed in claim 1 which is a hand cleaning or surface cleaning composition.

11. A topical gel formulation as claimed in claim 1 wherein the drug resistant bacterium is a Methicillin resistant *Staphylococcus aureus* (MRSA).

12. A topical gel formulation as claimed in claim 1 having antibacterial activity against at least *Propionibacterium acnes*.

13. A topical gel formulation having antibacterial activity comprising a selectively purified extract from the root of a *Salvia* spp comprising the identified tanshinone compounds
   Cryptotanshinone,
   Dihydrotanshinone,
   Tanshinone I, and
   Tanshinone IIA,
   said extract characterized in that the extract has antibacterial activity at a level of 16 micrograms per milliliter or less in the gel formulation and the selectively purified extract comprises 34.31 to 51.47% by weight of the identified tanshinone compounds and has a cryptotanshinone content of 15.16 to 22.74% by weight, a dihydrotanshinone content of 2.92 to 4.38% by weight, a tanshinone I content of 3.06 to 4.58% by weight, and a tanshinone IIA content of 13.18 to 19.76% by weight all based on the total weight of the extract; and said extract has antibacterial activity against at least one drug resistant bacterium.

14. A topical gel formulation comprising the extract as claimed in claim 13 wherein the extract has an HPLC fingerprint substantially as illustrated in FIG. 13.

15. A topical gel formulation comprising the extract as claimed in claim 13 which is a hand cleaning or surface cleaning composition.

16. A topical gel formulation comprising the extract as claimed in claim 13 wherein the drug resistant bacterium is a methicillin resistant *Staphylococcus aureus* (MRSA).

17. A topical gel formulation comprising the extract as claimed in claim 13 wherein the formulation has antibacterial activity against at least *Propionibacterium acnes*.

18. A topical gel formulation comprising the extract as claimed in claim 13 wherein the formulation has antibacterial activity against coagulase negative Staphylococci.

19. A topical gel formulation comprising the extract as claimed in claim 13 wherein the formulation has antibacterial activity against Streptococci.

20. A topical gel formulation comprising the extract as claimed in claim 19 wherein the formulation has antibacterial activity against *Streptococcus pneumoniae*.

* * * * *